Figure 1:
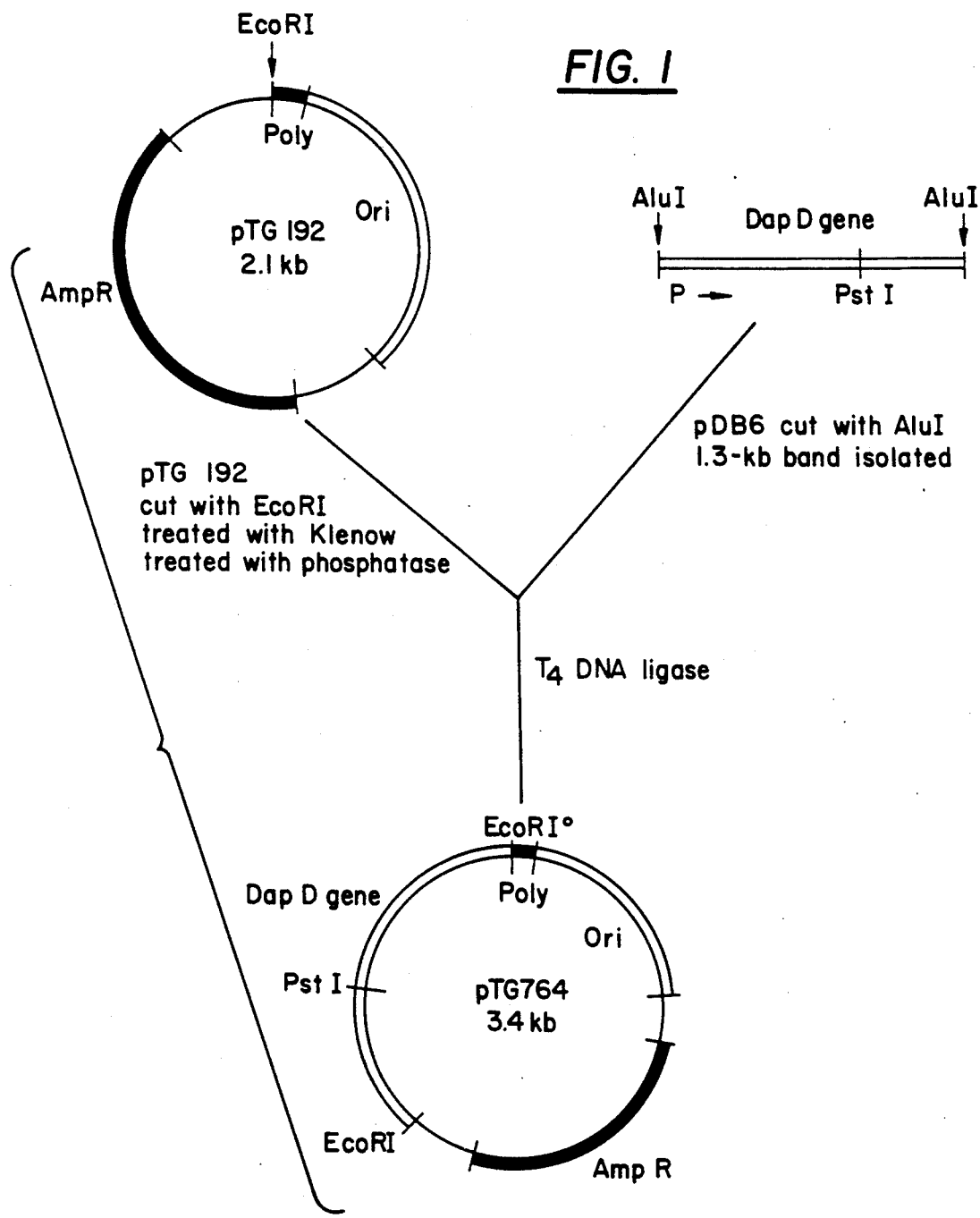

United States Patent [19]

DeGryse

[11] Patent Number: 5,198,343

[45] Date of Patent: Mar. 30, 1993

[54] METHOD FOR EXPRESSING A HETEROLOGOUS PROTEIN IN A DAPD⁻ MUTANT OF E. COLI AND THE STRAIN OBTAINED

[75] Inventor: Eric DeGryse, Strasbourg, France

[73] Assignee: Transgene, S.A., Courbevoie, France

[21] Appl. No.: 387,017

[22] Filed: Jul. 31, 1989

Related U.S. Application Data

[63] Continuation of Ser. No. 81,447, Aug. 4, 1987, abandoned.

[30] Foreign Application Priority Data

Aug. 5, 1986 [FR] France ............................ 86 11311
Jul. 15, 1987 [FR] France ............................ 87 09935

[51] Int. Cl.⁵ ..................... C12P 21/02; C12P 19/34;
C12N 15/00; C12N 7/00; C12N 1/21; C07H 15/12; C07K 3/00
[52] U.S. Cl. ..................... 435/69.1; 435/91;
435/172.3; 435/252.33; 435/320.1; 435/235.1;
536/23.1; 536/23.5; 536/23.52; 536/23.7;
536/23.2; 530/350; 935/10; 935/19; 935/23;
935/27; 935/42; 935/56; 935/73
[58] Field of Search ............... 435/69.1, 91, 172.1,
435/172.3, 252.33, 320.1, 235.1; 536/27; 935/9,
19, 23, 27, 42, 56, 73

[56] References Cited

U.S. PATENT DOCUMENTS 4,762,791 8/1988 Goeddel et al. ................... 435/243

FOREIGN PATENT DOCUMENTS 0185512 6/1986 European Pat. Off. .
8115385 7/1981 France .

OTHER PUBLICATIONS

Harvey et al Proc. Natl Acad. Sci, USA vol. 83 pp. 1084–1088 (1986).
Shevchenko et al, Chemical Abstracts vol. 100 Abstract No. 20447(f) 1984.
Richaud et al J. Biol. Chem. vol. 259, p. 14824 (1984).
Bollen et al. DNA vol. 2 pp. 255–264 (1983).

Primary Examiner—Joan Ellis
Attorney, Agent, or Firm—Cushman, Darby & Cushman

[57] ABSTRACT

The present invention relates to a method for the stabilization of a plasmid vector contained in a bacterium, wherein the bacterium comprises a dap⁻ chromosomal mutation and wherein the plasmid vector carries a dap⁺ gene.

6 Claims, 16 Drawing Sheets pDB6:

Hind III - BamHI fragment

METHOD FOR EXPRESSING A HETEROLOGOUS PROTEIN IN A DAPD− MUTANT OF *E. COLI* AND THE STRAIN OBTAINED

This is a continuation of application Ser. No. 07/081,447, filed Aug. 4, 1987, now abandoned.

The practical application of recombinant DNA technology to the production of molecules of interest by microorganisms generally runs into the problem of the instability of the recombinant plasmids.

Cloning and expression vectors commonly used in the laboratory are generally multicopy plasmids, and their stable transmission to the progeny is assured by the large number of plasmids per cell genome (Jones et al. 1980). However, the introduction of foreign genes into these plasmids gives rise to various degrees of instability during the multiplication cycles of the bacteria. Thus, industrial production operations may require 1,000-liter cultures, resulting in more than $10^{16}$ cells, after more than 50 generations. Therefore, it is essential to stabilize the plasmids in the bacteria in order to ensure their presence, and therefore the expression of the foreign molecule, until the end of the culture in the fermenter.

The stabilization of plasmids by integrating a gene coding for resistance to an antibiotic is a conventional laboratory practice which cannot, however, be applied to an industrial scale use for several reasons:

the use of an antibiotic-resistant bacterial strain may represent a risk to the environment;

the quantity of antibiotic required during the culture significantly increases the cost of production; and the use of an antibiotic cannot be envisaged in the production of substances to be used in human or veterinary therapy.

Therefore, it is essential to develop other methods for the selection of bacteria carrying a recombinant plasmid. The few models which have already been applied are based on the same principle: the host cell is made to undergo mutation (auxotrophic mutation or introduction of a gene which is lethal to the bacterium) so as to prevent it from multiplying in the absence of a plasmid coding for a character which makes up for the deficiency of the host.

For example, Skogman and Nilson (1984 and 1985) have used the complementation of a heat-sensitive val S mutation by the val S gene carried by a plasmid; in this model, the stability of the plasmid, which carries the tryptophan operon, is total after 200 generations at non-permissive temperature, whereas under non-selective conditions (30° C.), a plasmid loss of 1.2% is observed in each generation.

Miwa et al. (1984) have used, as the host strain, a streptomycin-dependent ($Sm^d$) *E. coli* mutant and a plasmid carrying a gene (rpsl of an $Sm^R$ strain) which masks the $Sm^d$ phenotype and renders the strain independent of streptomycin, thereby ensuring a plasmid stability greater than 99%.

Herthberger and Rosteck (1984) have rendered a bacterium lysogenic for a prophage lambda whose repressor has been deleted; the cell can escape lysis only in the presence of a plasmid carrying the lambda cI repressor.

A new selection model has been developed, based on the complementation of a dap− chromosomal mutation with a dap+ plasmid gene, which ensures the survival of only the plasmid-carrying cells.

Diaminopimelic acid (DAP) is a component of bacterial cell walls; it is also an intermediate in the biosynthesis of lysine from aspartate. A strain which is deficient in an enzyme for DAP biosynthesis will not be able to multiply in a minimal medium; the addition of lysine to the medium will permit growth, but will soon bring about the lysis of the cell which does not incorporate DAP in its membrane (Work 1950—Davis et al., 1973).

The deficiency of an enzyme for DAP biosynthesis may be compensated for by the introduction of the corresponding gene on a plasmid and, in particular, on the expression vector of the foreign protein required to be produced. If the bacterium loses the plasmid, it becomes dap− and can no longer multiply. This model has the advantage that it can be applied to any DAP-free culture medium, i.e. any medium for industrial-scale production and any medium, rich or minimal, to which lysine has been added.

The system also has the advantage of not interfering with the synthesis of DNA, RNA or proteins.

A dapD− strain (with one of the 9 genes of the biosynthetic pathway of lysine, the gene D, corresponding to tetrahydropicolinate-N-succinyl transferase, deleted) is constructed and the dapD gene on a commonly used expression plasmid (carrying the gene to be expressed under the control of the promoter $P_L$) is introduced. Under selection conditions, it can be shown that the plasmid is stable for at least 150 generations.

The cloning of another gene (dapA), coding for an enzyme for the biosynthesis of lysine, on a plasmid, has already been carried out, with a view to increasing the production of lysine (Dauce-Le Reverend et al. 1982); however, these authors have not been able to control the stability of their plasmid.

The dapD gene of *E. coli* has already been cloned into the plasmid pBR322 and its nucleotide sequence has been published by Richaud et al. (1984); however, the object of this work is only to study the regulation of this gene.

For this reason, the present invention relates to a method for stabilizing a plasmid vector contained in a bacterium, wherein the bacterium comprises a dap− chromosomal mutation and wherein the plasmid vector carries a dap+ gene.

Among dap− chromosomal mutations, dapD− will preferably be employed; however, other genes coding for an enzyme for DAP biosynthesis could also be employed, on condition that a vector plasmid carrying the corresponding gene is used; in the case of a dapD− strain, the gene to be inserted into the plasmid will be dapD.

The dap stabilization system does not interfere with the expression of the protein, it may therefore be used with any expression vector.

In order to avoid possible homologous recombinations between the dapD+ plasmid and the mutated dapD gene of the chromosome, it is preferable to provide for a substantial deletion of the dapD gene from the chromosome.

For this reason, the present invention relates more particularly to a method for the stabilization of a plasmid vector contained in a bacterium as described above, wherein the dap chromosomal mutation is a deletion of at least a portion of the dapD gene and wherein the plasmid vector carries an intact dapD gene.

It is clear that in order to avoid any recombination, a total deletion of the dapD gene will be the most satisfactory solution.

However, a selection system, however strong it may be, cannot overcome the inherent instability of a plasmid. Because of this, in order to increase the stability of the expression vectors in question by genetic means it is possible to introduce into said vectors a sequence which maintains them in the monomeric state, especially the "cer" sequence.

The "cer" (Summers and Sherratt, 1984) is an element which does not code for any protein and the presence of which promotes the maintenance of a plasmid in the monomeric state. If the plasmid forms multimers, the number of units which can be distributed to daughter cells drops and plasmid-free cells are obtained more easily. Therefore, cer stabilizes the plasmid indirectly by maintaining it in the monomeric state.

For this reason, the present addition also relates to plasmid vectors which additionally comprise the gene coding for a protein of industrial value and to the elements which ensure its expression in the host bacterium and, in particular, to the gene coding for a hirudin or one of the natural or synthetic variants thereof, for example, $C_{2,3}O$, interferon-gamma or alpha-antitrypsin, and to strains transformed by these different vectors and to the methods for the preparation of industrial proteins by culturing said transformed strains in a complete medium and recovering the protein after culture.

In the following text, the expression system comprises the leftward promoter, $P_L$, of phage lambda; however, it could be another promoter which is active in the bacterium in question. This explains the reason for not giving a complete description of the expression elements of the heterologous protein, this type of plasmid now being widely known. It will be advisable simply to insert the dapD or other gene into a non-essential site of the plasmid vector.

The plasmids in question may be employed to transform any E. coli strain which has been rendered dapD$^-$.

By virtue of the method according to the invention, bacterial strains in which the expression plasmids are stable in a complete medium without the need, for example, for a selection pressure by an antibiotic or for a specific amino acid-free medium, are obtained. Additionally, the method according to the invention exerts a counter selection against bacteria which have lost the plasmid.

Therefore, the invention also relates to bacterial strains, in particular dap$^-$ E. coli, transformed by a plasmid vector carrying a dap$^+$ gene and to elements which ensure the expression of a protein of industrial value, carried by this plasmid.

The invention also relates to a method for the preparation of a protein of industrial value from a bacterium, wherein a bacterium transformed by a plasmid according to the invention is cultured in a complete medium, said plasmid additionally comprising the gene of said protein and control signals for the expression of this protein in the host bacterium.

The object of the examples below is to demonstrate the stability of plasmids carrying the dapD gene in the dap$^-$ bacteria, in comparison with plasmids carrying the Amp$^r$ gene.

Additionally, these plasmids carrying the dapD gene have been used to express the genes coding for hirudin and interferon-gamma.

These two genes are placed under the control of the phage lambda promoter $P_L$ and the E. coli host strains contain the heat-sensitive repressor CI857; this system makes it possible to induce the expression of the gene controlled by $P_L$ by increasing the temperature.

The E. coli strain TGE 900 which contains the repressor CI857 was modified to become dapD$^-$ by giving the strain TGE 7615.

Figure 2:
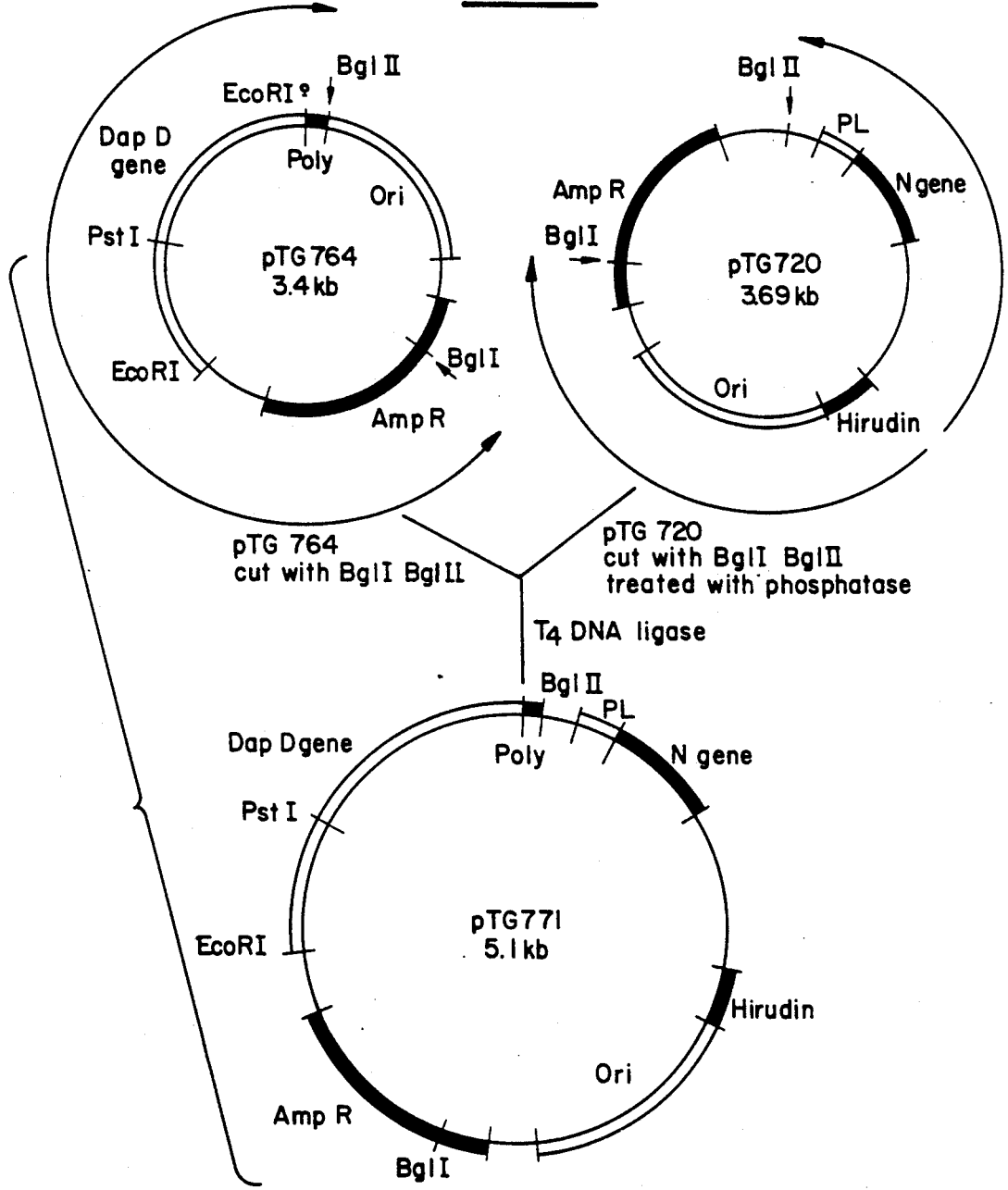
Figure 3:
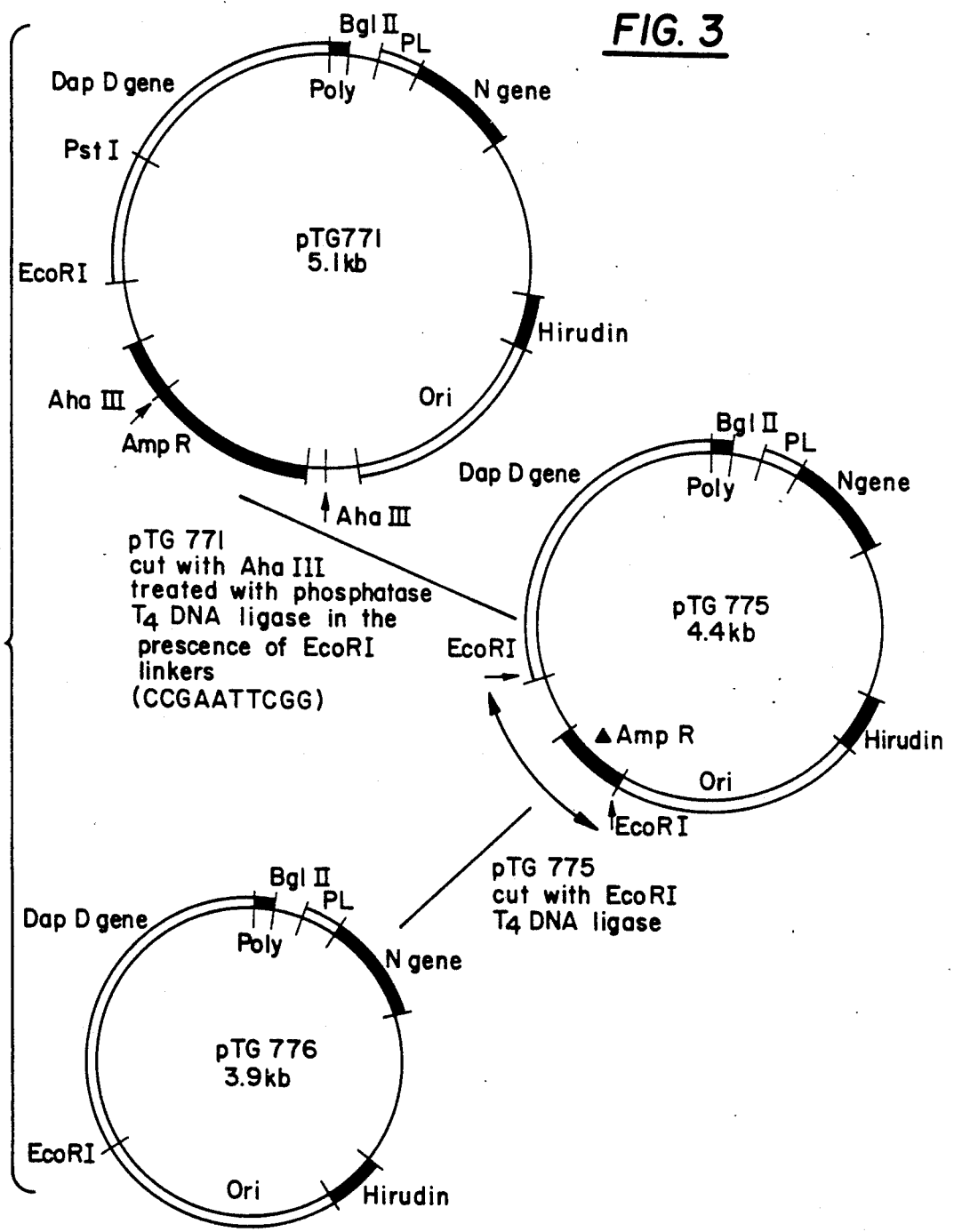
Figure 4:
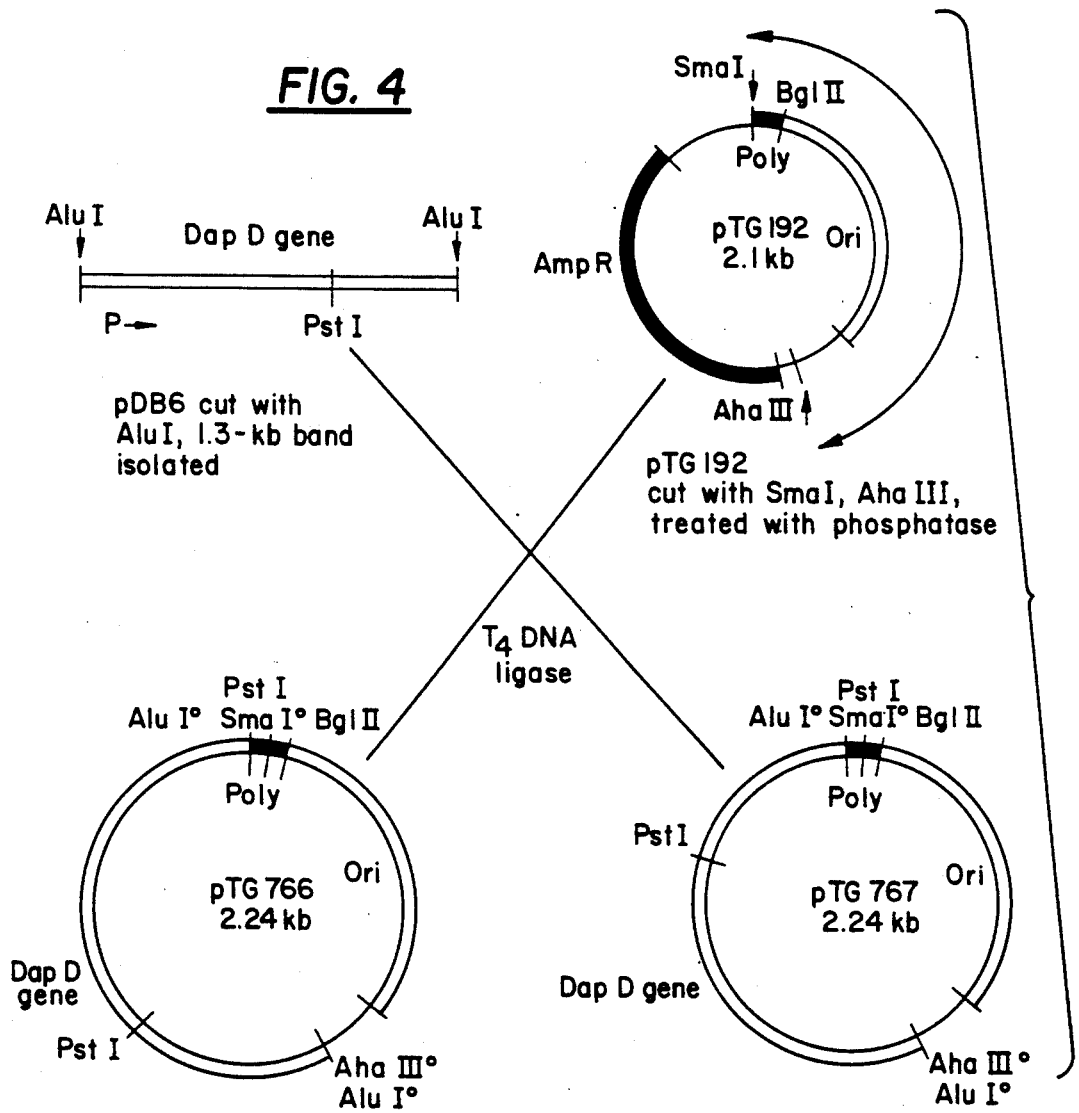
Figure 5:
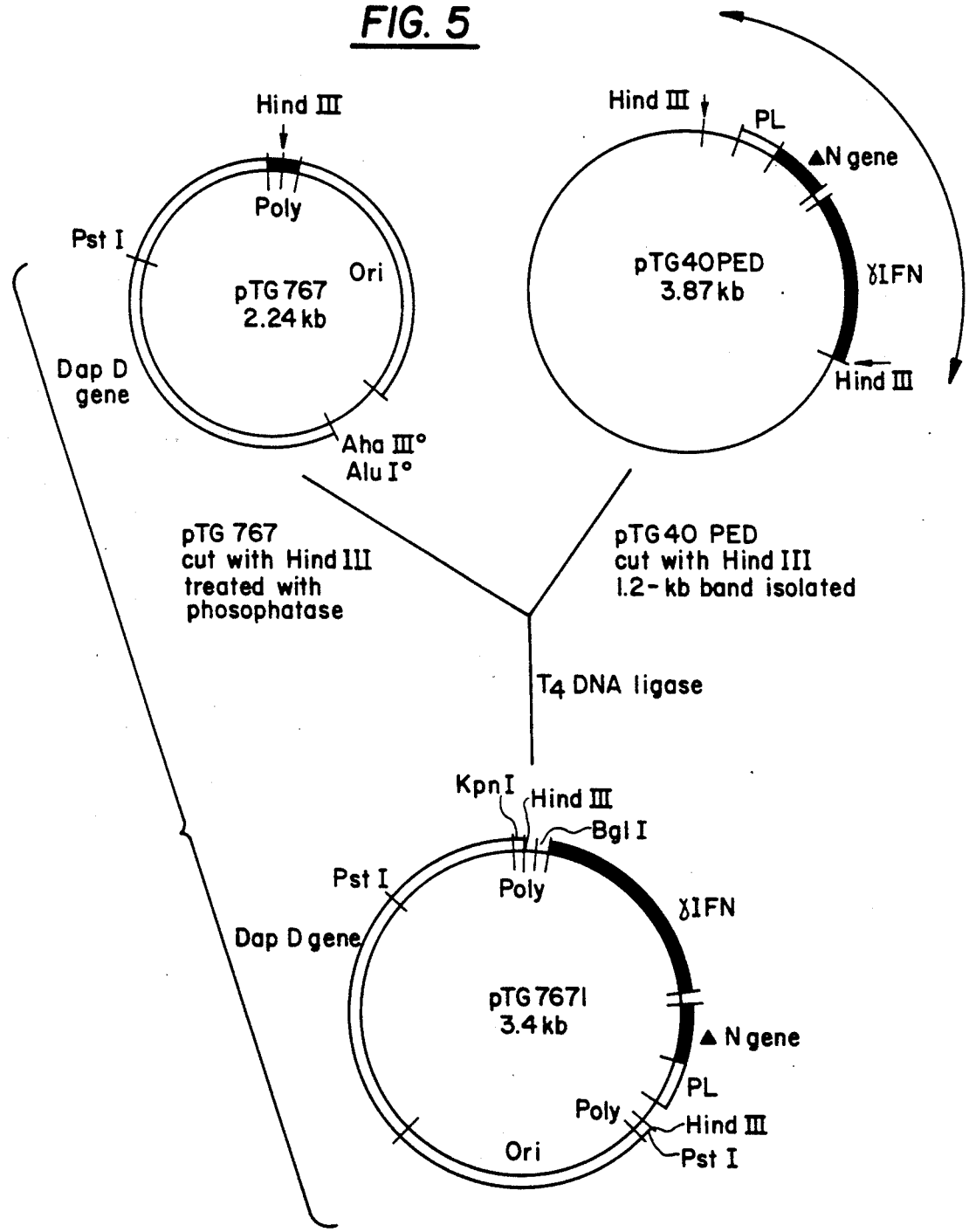

The following plasmids were then prepared according to the diagrams attached hereto:

|  | Amp$^r$ | dapD | Foreign protein |
|---|---|---|---|
| FIG. 1 - pTG764 | + | + | 0 |
| FIG. 2 - pTG720 | + | 0 | Hirudin |
| FIG. 2 - pTG771 | + | + | Hirudin |
| FIG. 3 - pTG775 | 0 | + | Hirudin |
| FIG. 3 - pTG776 | 0 | + | Hirudin |
| FIG. 4 - pTG766 | 0 | + | 0 |
| FIG. 4 - pTG767 | 0 | + | 0 |
| FIG. 5 - pTG7671 | 0 | + | IFN-gamma |
| FIG. 5 - pTG7672 | 0 | + | IFN-gamma |

Figure 6:
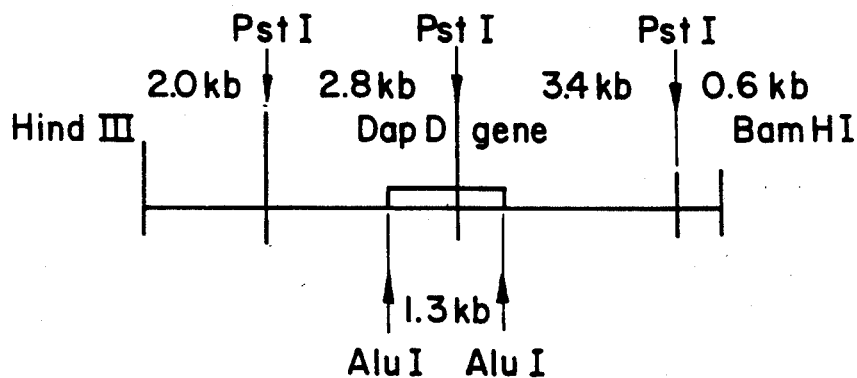

FIG. 6: Restriction map of the HindIII-BamHI fragment of pDB6.

Figure 7:
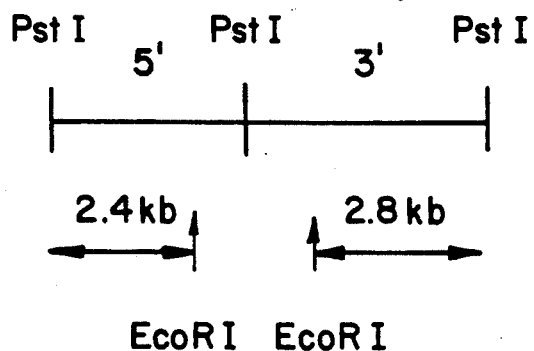

FIG. 7: Diagram of PstI inserts of pDB6 in M13mp8 and position of EcoRI sites introduced therein.

Figure 8:
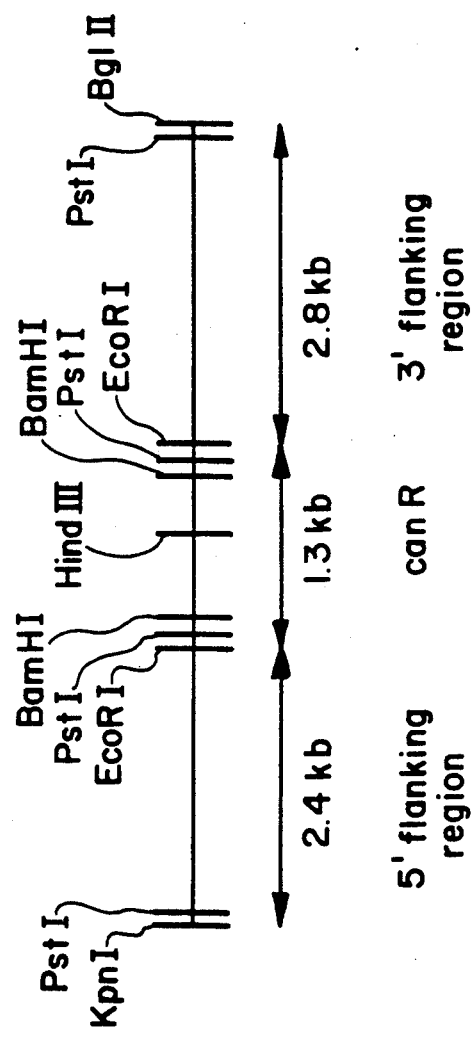

FIG. 8: Restriction map for the KpnI-BglII fragment of pTG47.

FIG. 9: Demonstration of the deletion of the dap gene in chromosomal DNAs of different strains, by "Southern blot" autoradiography.

Figure 9A:

FIG. 9A: probe=kan$^R$ gene carried by the EcoRI fragment of pTG47

| bands 6 to 9 | DNA cut with PstI |
|---|---|
| 10 to 14 | DNA cut with BamHI and HindIII |
| bands 6 and 10 = | strains GC4540 |
| 7 and 11 | TGE7213 |
| 8 and 12 | TGE7214 |
| 9 and 13 | TGE901 |
| 14 | pDB6 |
| 1, 2, 5, 16 | molecular weight markers |

Figure 9B:
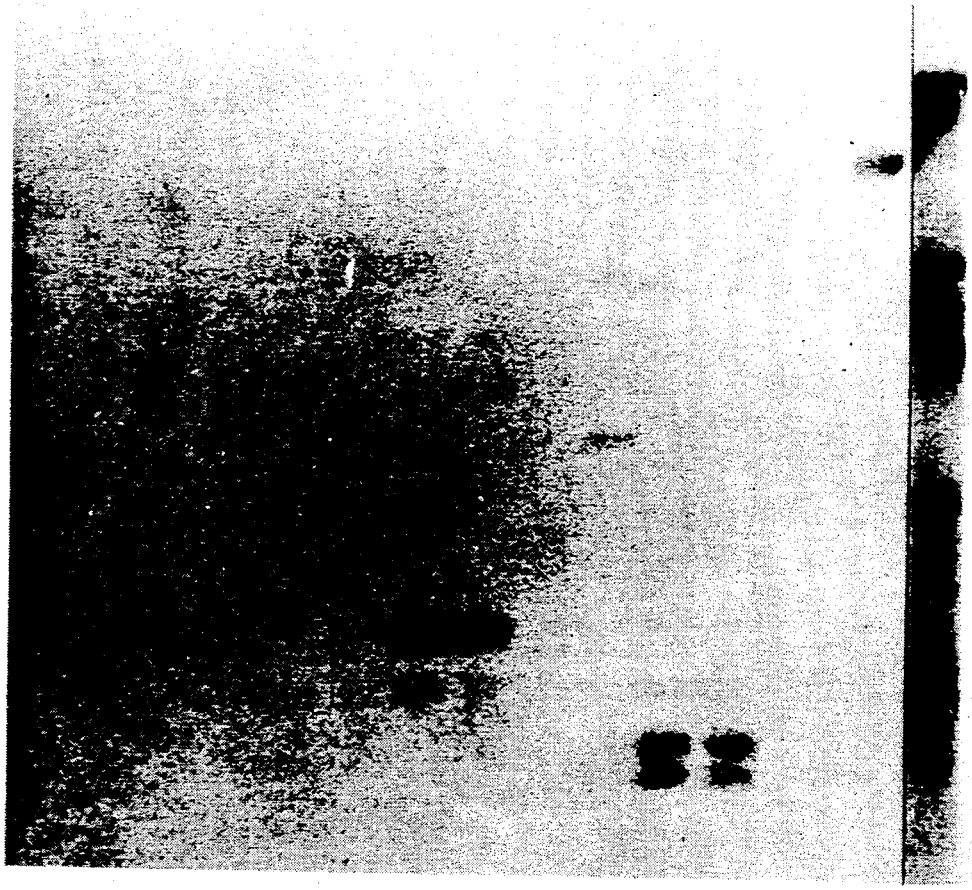

FIG. 9B: probe=5' side of the dapD gene carried by the EcoRI fragment of M13TG620

| bands 4 to 7 | DNA cut with PstI |
|---|---|
| 8 to 11 | DNA cut with BamHI and HindIII |
| bands 4 and 8 = | strains GC4540 |
| 5 and 9 | TGE7213 |
| 6 and 10 | TGE7214 |
| 7 and 11 | TGE901 |
| bands 13 | molecular weight markers |
| 1 and 12 | pDB6 cut with PstI or BamHI and HindIII |
| 2 | M13TG620 cut with PstI |
| 3 | M13TG597 cut with PstI |

Figure 9C:

FIG. 9C: probe=flanking regions of the dapD gene carried by the KpnI-BglII fragment of pTG47.

| Chromosomal DNAs cut with PstI. | | |
|---|---|---|
| bands 4 = | strains | GC4540 |
| 5 | | TGE7213 |
| 6 | | TGE7214 |
| 7 | | TGE901 |
| bands 8 = | molecular weight markers | |
| 1 | BamHI-HindIII fragment of pDB6 cut with PstI | |
| 2 | M13TG620 cut with PstI | |

-continued

| Chromosomal DNAs cut with PstI. | |
|---|---|
| 3 | M13TG597 cut with PstI |

Figure 9D:

FIG. 9D: probe=flanking regions of dapD gene carried by the KpnI-BglII fragment of pTG47.

| Chromosomal DNAs cut with PstI. | |
|---|---|
| bands 4 = | strains RH5345 |
| 5 | RL58 |
| 6 | TGE7615 |
| 1, 2 and 3 (as in 9C) | |

Figure 10:
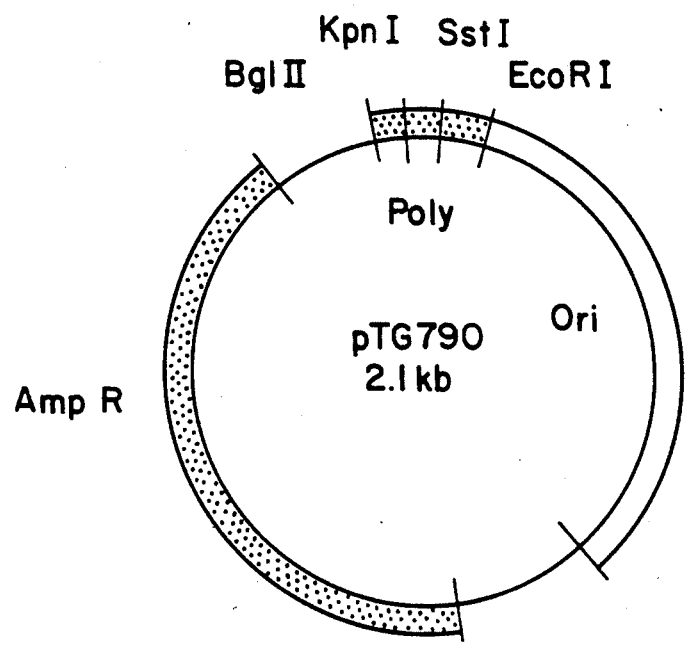
Figure 11:
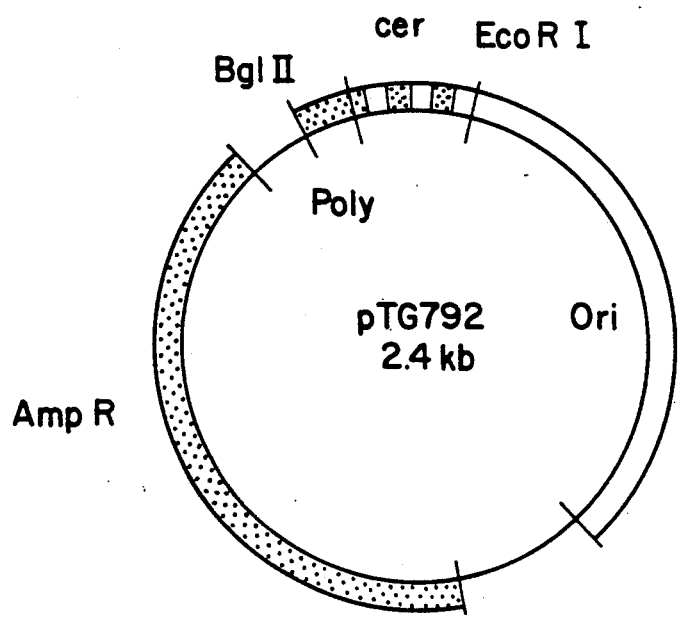
Figure 12:
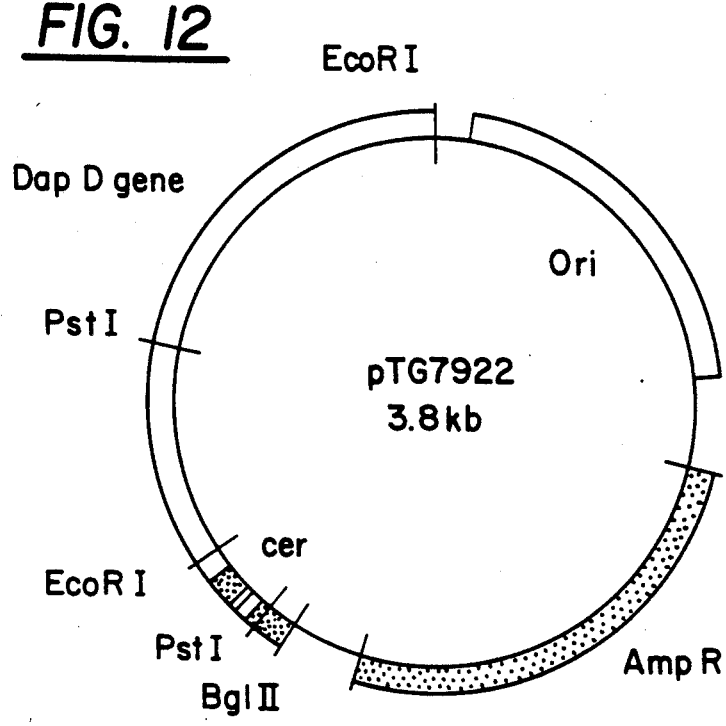
Figure 13:
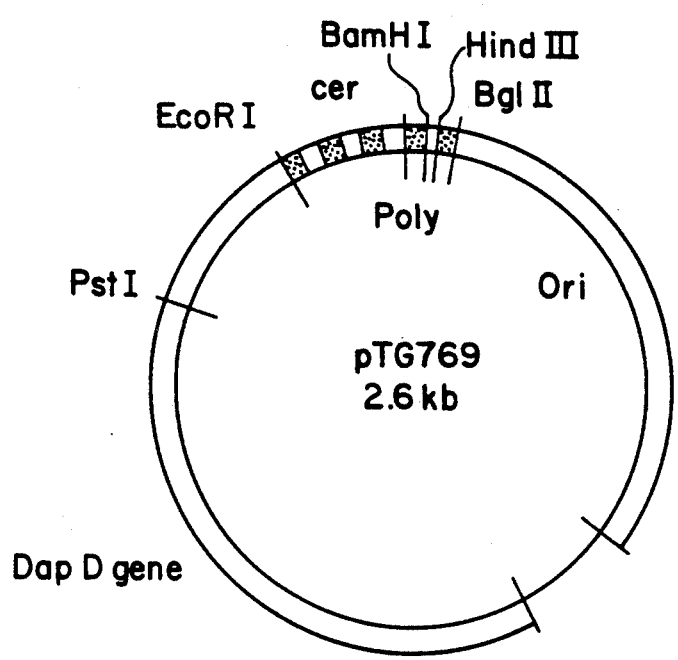
Figure 14:
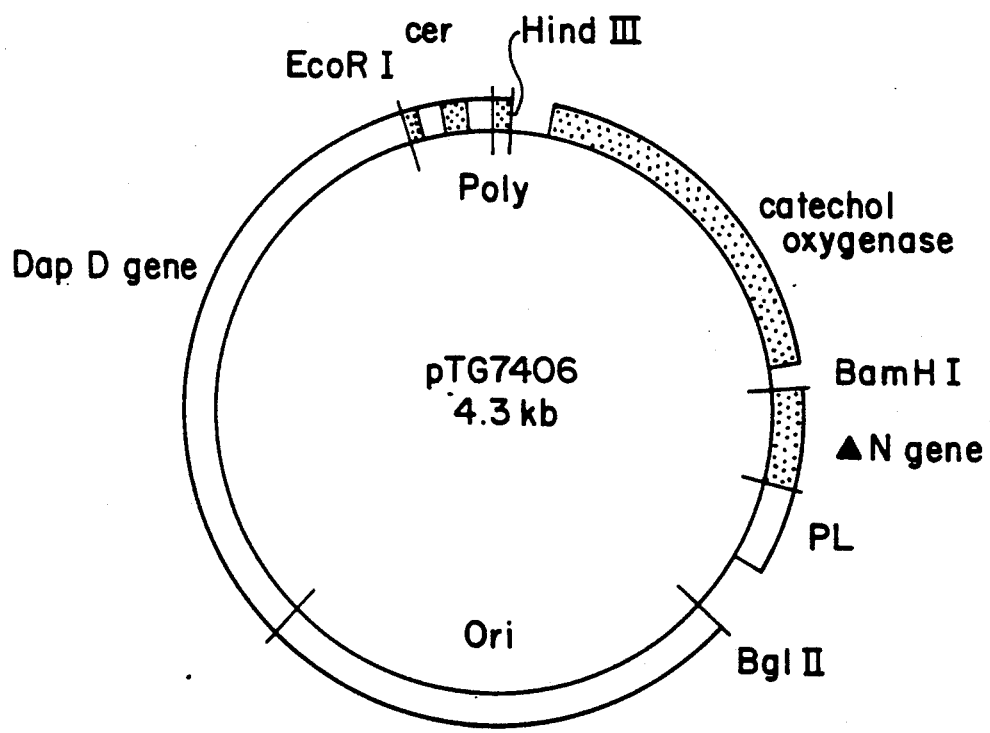
Figure 15:
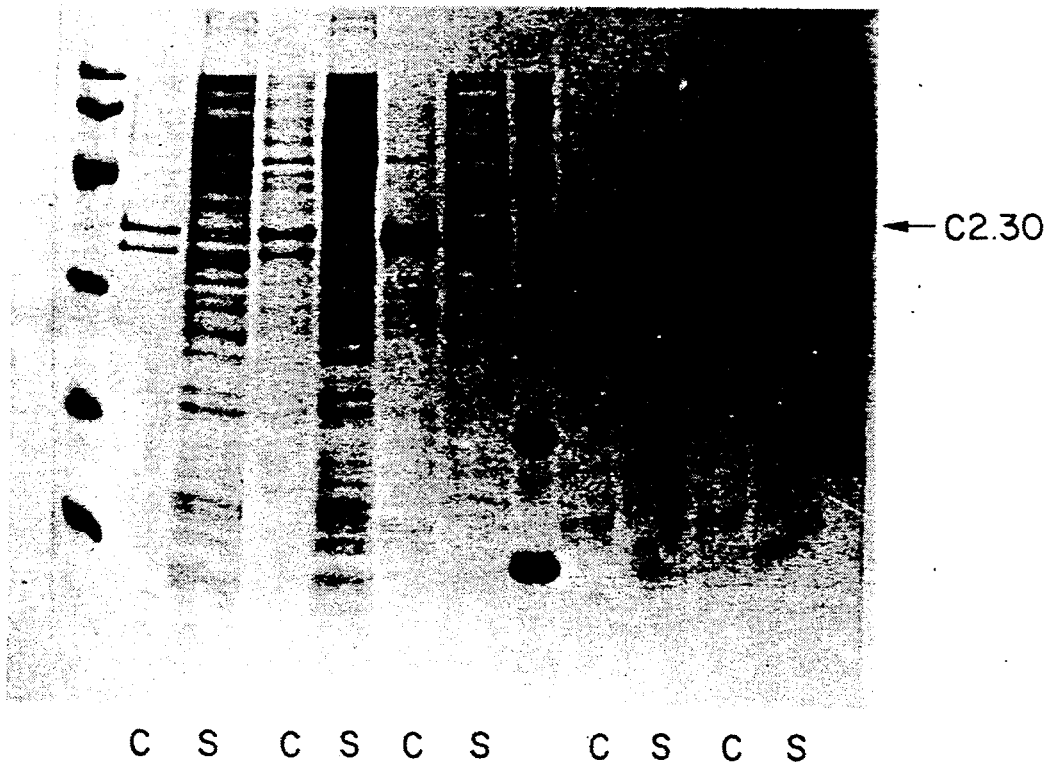
Figure 16:
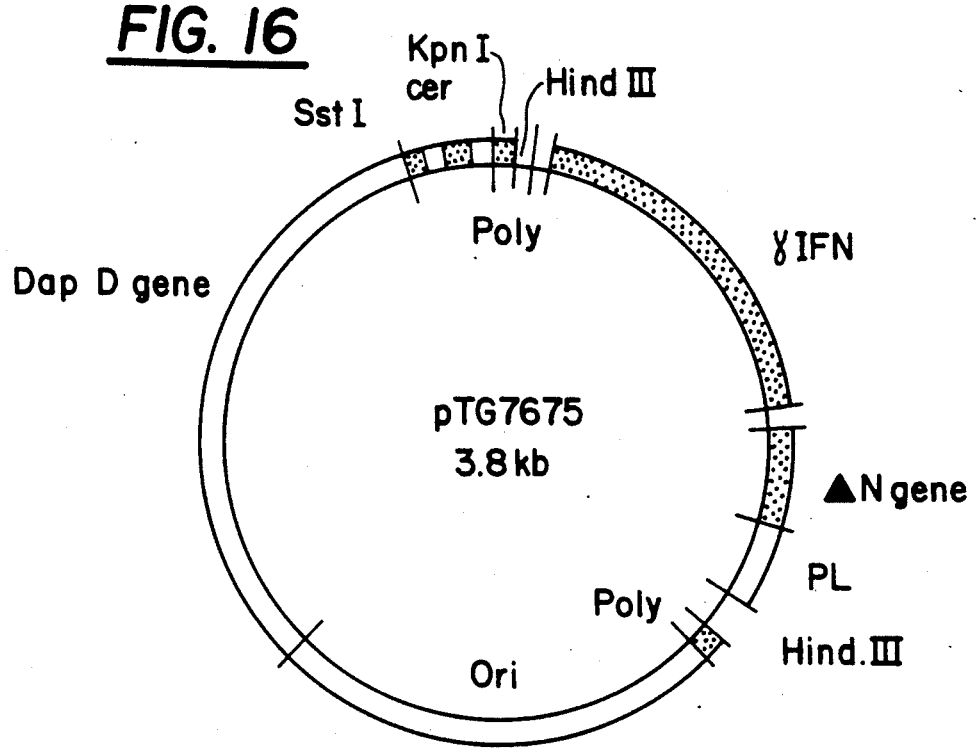
Figure 17:
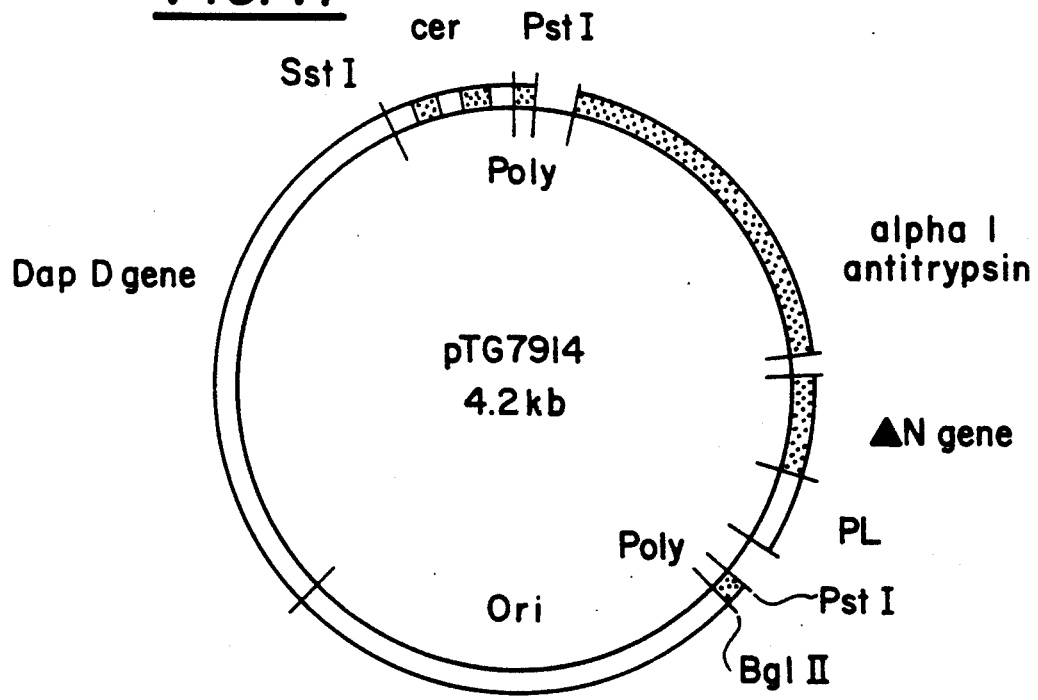

FIG. 10: Diagram and restriction map for pTG790.
FIG. 11: Diagram and restriction map for pTG792.
FIG. 12: Diagram and restriction map for pTG7922.
FIG. 13: Diagram and restriction map for pTG769.
FIG. 14: Diagram and restriction map for pTG7406.
FIG. 15: SDS polyacrylamide gel electrophoresis, visualized with Coomassie blue, of proteins synthesized by TGE7213/pTG7407.
  bands 1 and 8=molecular weight markers
  bands 2 to 5=culture at 30° C. for 4 hours (2 and 3) or 7 hours (4 and 5)
  bands 6 to 12: culture initiated at 42° C. for 4 hours (6, 11 and 12) or 7 hours (7, 9 and 10)
  C=insoluble fractions; 20 μl
  S=soluble fraction; 40 μl
FIG. 16: Diagram and restriction map for pTG7675.
FIG. 17: Diagram and restriction map for pTG7914.

METHODS

Unless otherwise mentioned, the different enzymes are employed according to known techniques.

Transformation

Competent cells were prepared according to the method of Hanahan (1983). Their competence ranges up to $10^4$ to $10^5$ transformants/μg DN for the RL58 strain (Bollen et al. 1979) and $10^5$ to $10^6$ transformants/μg DN for the TGE 7615 strain.

In general, 1 to 10 μl of a solution, at the appropriate dilution, of a DNA preparation containing the plasmid which is desired to be introduced into the strain, is added to 0.2 ml of a stock of competent cells. The cells are allowed to react with the DNA for 15 minutes at 0° C. and they are then incubated at 37° C. for 90 seconds. They are returned to 0° C. for 5 minutes and then 0.8 ml of LB medium is added thereto. For the strain RL58 or for the strain TGE 7615, this medium must contain DAP at a rate of 8 gamma/ml. This is necessary for the growth of dapD$^-$ cells, even for those which contain the plasmid carrying the dapD gene. The cells are generally incubated at 30° C., with vigorous stirring (however, they may be placed at 37° C. if the plasmid does not contain the promoter $P_L$). The incubation period is 60 minutes, but it can be extended to 90 minutes for growth at 30° C. for the strain TGE 7615.

Subsequently, defined volumes (0.1 ml) are spread on solid LB medium. In the case of plasmids containing the gene for ampicillin resistance, the clones are selected by adding 100 gamma/ml of ampicillin; the clones containing the dapD gene are selected from a culture which is dapD$^-$ on the whole, on the LB medium without other additions. The dishes are incubated for 24 hours at 30° C. The colonies are then transferred with toothpicks into 3 ml of LB medium and, after growth at 30° C. overnight, the plasmid is isolated and its structure confirmed on agarose gel, after digestion with appropriate restriction enzymes.

Plasmids containing the dapD gene may be transformed in any E. coli which carries the dapD$^-$ mutation (for example RL58, TGE7615); if they additionally contain the bacteriophage lambda promoter $P_L$, they must necessarily be transformed in dapD$^-$ E. coli strains which express the bacteriophage lambda repressor cI857 either on a plasmid or in the chromosome, or cI and Rec mutation (for example RecA441).

EXAMPLE 1

Introduction of a mutated dapD$^-$ gene in E. coli strain TGE900

The E. coli host strain TGE900 was rendered dap$^-$ by conjugation with a known dapD$^-$ mutant, RL58.

The strain TGE900 is a derivative of strain N4830 described by Gottesman et al. (1980), the characteristics of which are as follows: su$^-$ F$^-$ his ilv bio (λ cI857 Δ Bam Δ HI)Sm$^r$. It is commonly used as the host for expression vectors in which the foreign gene is placed under the control of the lambda promoter $P_L$ as it enables the expression to be induced at will by increasing the temperature (above 37° C.), which inactivates the heat-sensitive repressor (lambda cI857) carried by the bacterium.

The dap$^-$ RL58 (met B dapD$_2$ met D279 Hfr P$_4$ X) strain has been described by Bollen et al. (1979).

Starting with this strain, a trimethoprim-resistant spontaneous mutant was selected (after spreading the strain on a dish containing 2 gamma/ml of trimethoprim and confirming the resistance of a colony chosen from a medium containing 4 gamma/ml trimethoprim). In fact, the gene coding for this resistance is sufficiently close to the dapD$^-$ mutation so that if the recipient strain, after conjugation, becomes resistant to trimethoprim, it also becomes dapD$^-$.

The resistant strain has been called TGE755; the useful characteristics thereof are: Hfr dapD$^-$ Tmp$^r$.

After conjugation of the strains TGE900 (F$^-$ Sm$^{res}$ dap$^+$), and TGE755, stopped after 15 minutes, by spreading on a minimal medium containing DAP, streptomycin and trimethoprim, Sm$^r$ Tmp$^r$ colonies are selected; the dap$^-$ nature of the strains selected and the presence of auxotrophic mutations in the parent strain (his ilv val) in the minimal medium containing DAP, are verified on an LB medium.

One strain (his ilv dap$^-$) was chosen: TGE7615.

EXAMPLE 2

Construction of a vector plasmid carrying the E. coli dapD gene (FIG. 1)

a) Construction of a multiple-use cloning plasmid comprising a polylinker with 12 restriction sites The construction was initiated starting with a pML$_2$ plasmid (Lusky and Botchan, 1981), derived from pBR322 by deleting the nucleotides 1089 to 2491. This plasmid retained the origin of replication of pBR322 and the beta-lactamase gene (ampicillin resistance).

The PstI enzyme recognition sequence was removed by inserting an AhaIII—AhaIII fragment of pUC8 which carries a PstI$^o$ mutation induced with ethanesulfonate (Vieira and Messing, 1982), between the two AhaIII sites of pML$_2$, which deletes 19 base pairs from pML2. The resulting plasmid, pTG190, carries the PstI° mutation of pUC8.

A BglII linker (5'-dCAGATCTG-3'; Collaborative Research) was inserted into the only NruI site, by the "linker tailing" technique described by Lathe et al., 1984. The resulting construction is pTG191.

The pTG191 was opened with EcoRI and BglII (which deletes the tetracycline-resistance gene) and religated with the EcoRI-BglII segment of phage M13TG131 (Kieny et al., 1983) which comprises a polylinker containing 12 restriction enzyme recognition sequences.

The resulting plasmid is pTG192.

b) Cloning of a dapD gene in the pTG192 plasmid

The dapD chromosomal gene of E. coli was inserted into the plasmid pACYC184 to give pDB6 (Bendiak and Friesen, 1981). This dapD gene was recovered from pDB6 in the form of a 1.3-kb AluI fragment and inserted into the EcoRI site of pTG192 (the EcoRI ends having been repaired beforehand by treating with the Klenow fragment of DNA polymerase I).

From the resulting plasmids, pTG764, in which a single EcoRI site is reconstituted, is chosen. Thus, the pTG764 carries the dapD gene and the ampicillin-resistance gene of pTG192 (originally of pUC8).

EXAMPLE 3

Expression plasmid of hirudin containing dapD and $Amp^r$ genes (FIG. 2)

The pTG720 plasmid described in French Patent No. 84/04,755 essentially comprises the hirudin gene under the control of the lambda promoter $P_L$.

The pTG720 plasmid, digested with BglII and BglI, gives a 2.74-kb fragment which carries the hirudin gene and a portion of the $amp^r$ gene. This fragment, treated with phosphatase, is religated to the BglII-BglI fragment of the pTG764 plasmid which carries the dapD gene and another fragment of the $amp^r$ gene. The resultant plasmid, pTG771, carries the reconstituted whole $amp^r$ gene, the dapD gene and the gene coding for hirudin.

The colonies of TGE7615 transformed by this plasmid may be selected either on an LB medium (selection for the dap+ nature) or on an LB+ampicillin medium.

After induction, the transformed strain produces hirudin.

EXAMPLE 4

Expression plasmid of hirudin containing the dapD gene and no longer containing the $Amp^r$ gene (FIG. 3)

The starting plasmid is pTG771.

A digestion is carried out with AhaIII in order to remove the small fragment comprising the 3' end of the gene coding for $Amp^r$ and the plasmid is closed again by ligation in the presence of an EcoRI "linker":

CCGAATTCGG

The pTG775 plasmid is obtained.

An EcoRI digestion followed by ligation enables the gene coding for $Amp^r$ to be removed completely.

The pTG776 plasmid is obtained.

The TGE7615 bacteria transformed by this plasmid may be selected on an LB medium, without addition (selection for the dap+ character).

After induction, the transformed strain produces hirudin.

EXAMPLE 5

Construction of plasmids carrying the dapD gene and not containing the $Amp^r$ gene (FIG. 4)

The starting plasmid is the plasmid pTG192.

After digesting with SmaI and AhaIII and then treating with phosphatase, the 0.95-kb vector fragment is isolated and ligated with the 1.3-kb AluI fragment of pDB6 which carries the dapD gene. The $amp^r$ gene has therefore been completely deleted. The TGE7615 strain is transformed with this new plasmid and selection is carried out on an LB medium in order to obtain clones which carry the dapD gene.

Plasmids which carry the dap gene in the two orientations are obtained; the orientation of the insert may be determined by digesting with PstI. For two candidates chosen:

pTG766 releases 1.34-kb and 0.9-kb fragments, and pTG767 releases 1.85-kb and 0.4-kb fragments.

EXAMPLE 6

Expression plasmid of interferon-gamma, carrying the dapD gene (FIG. 5)

The pTG40 (PED) plasmid carries, on a 1.2-kb HindIII fragment, the interferon-gamma gene under the control of the promoter $P_L$. After digesting with HindIII, this fragment is recovered and inserted into the HindIII site of pTG767 which has previously been treated with phosphatase. After ligation, TGE7615 is transformed and selection for the presence of the dapD gene is carried out on an LB medium. Two plasmids carrying the insert in opposite orientations are chosen:

pTG7671 (which has the $P_L$ proximal of the replication origin and in the same orientation), and pTG7672.

The TGE7615 bacteria transformed by these plasmids may be selected on an LB medium, without addition (selection for the dap+ character).

After induction, the transformed strain produces interferon-gamma.

The following examples are intended to demonstrate the characteristics of the strains transformed according to the present invention.

All the plasmids carrying the dapD gene are in the TGE7615 strain and the others are in the TGE900 strain.

The stability of the different plasmids was tested in suitable media:

"selective medium" will refer to the LB medium in the case of the plasmids according to the invention and to the LB+ampicillin medium in the case of plasmids pTG720 and pTG740; and "non-selective medium" will refer to the LB medium+DAP in the case of the plasmids according to the invention and to the LB medium in the case of other plasmids.

A study of stability over 110 generations is carried out by several successive cycles of dilution and multiplication of the bacteria. At the end of this multiplication phase, the stability of the plasmid is determined as follows:

the number of viable cells in the culture is determined by suitable dilution and counting the cells in a non-selective agar medium; and at the same time, a significant sample of these colonies is transferred into selective and non-selective agar media, and the percentage of colonies which have lost the plasmid, and therefore the capacity to grow in a selective medium, is determined.

The results obtained with the plasmids carrying the interferon gene are given in Table I:

TABLE I

Determination of plasmid loss by bacteria after 110 generations

| Strain | TGE 900 | TGE7615 | TGE7615 | TGE7615 |
|---|---|---|---|---|
| Plasmid | pTG40 | pTG766 | pTG767 | pTG7671 |
| Selection | Amp | dapD | dapD | dapD |
| LB medium p−/c/generation* | $2 \times 10^{-3}$ | $<5 \times 10^{-5}$ | $<5 \times 10^{-5}$ | $3 \times 10^{-5}$ |
| LB medium + DAP | $2 \times 10^{-3}$ | $<5 \times 10^{-5}$ | $<5 \times 10^{-5}$ | $3 \times 10^{-5}$ |

*c = number of viable cells
p− = cells which have lost the plasmid
p−/c/generation = (number of p−/number of c tested) × number of generations Similar tests carried out with plasmids carrying the hirudin gene and with the cloning vector pTG766, after the multiplication of the bacteria over 170 generations in an LB medium, give the following results:

TABLE 2

Determination of plasmid loss by bacteria after 170 generations in an LB medium

| Strain | TGE900 | TGE7615 | TGE7615 | TGE7615 |
|---|---|---|---|---|
| Plasmid | pTG720 | pTG771 | pTG776 | pTG766 |
| p+ (%) | 96 | 98 | 100 | 100 |
| p−/c/generation | $2 \times 10^{-4}$ | $1.5 \times 10^{-4}$ | $<1.1 \times 10^{-4}$ | $<1.1 \times 10^{-4}$ |

The results presented in Tables 1 and 2 show that
1) the stability of dap vectors is increased by a factor of 10 relative to the plasmid carrying the amp$^r$ gene;
2) the difference between the selective and non-selective media is minimal;
3) the cloning vectors pTG766 and pTG767 have a loss of less than $5 \times 10^{-5}$ p−/c/generation;
4) the stability of pTG40 is significantly less than that of the dap+ vectors; however, it is worth pointing out that the phenomenon becomes particularly marked after 50 generations; at the early stages of culture, the loss is only $2.5 \times 10^{-4}$ p−/c/generation; and
5) the loss of amp$^r$ control plasmids pTG40 and pTG720, carrying the interferon and the hirudin genes respectively, is of the same order of magnitude; this plasmid loss with time is reduced when they carry the dapD gene (pTG766, 767, 7671 and 776).

However, it should be pointed out that the stability of the plasmid carrying the dapD gene and the gene for ampicillin resistance (pTG771) is lower and remains comparable to that of pTG720. This result is explained by an analysis of the plasmid content in the agarose gel; the latter shows that pTG771 forms tetramers, which phenomenon has repercussions on the partition of plasmids and which increases their loss (Summers and Sherratt, 1984). It should be added that over a smaller number of generations (30), this multimerization phenomenon does not take place, and that over a total of 70 generations, the loss of pTG771 remains less than $2.8 \times 10^{-4}$ p−/c/generation.

Therefore, the stability of the plasmids which contain the dapD gene is increased relative to the plasmids carrying the amp$^r$ gene, and their loss becomes minimal.

EXAMPLE 8

Stability of Plasmids at 37° or 42° C.

The effect of temperature on the stability of plasmids cannot be studied in the case of those which contain a gene coding for a foreign protein placed under the control of the promoter $P_L$ without inducing the expression of this foreign protein. Nevertheless, it should be pointed out that, under the operating conditions, the induction is followed by an increase in O.D. from 0.3 to 3.6, which corresponds to 3.6 generations. Therefore, in fact, the bacteria form the largest number of generations at 30° C., before induction, with a loss which has already been determined in the preceding example.

When the expression of a foreign protein is induced (for example hirudin for pTG720 and interferongamma for pTG40), a mortality of the E. coli culture, at a rate of 90% to 95%, is observed after a certain period of time (2 to 4 hours). These are cells containing the plasmid (because the p− host cell is capable of growing at 37° to 42° C.). Inevitably, this mortality increases the proportion of p− cells relative to the living cells by a factor of 10 to 20. When the total number of living cells is significantly decreased, and the p− cells form a significant fraction of the population, the multiplication of the p− cells is determined, which decreases significantly the p+/p− ratio (see for example Table 3, results obtained after 5 h 30 min and 7 hours).

It is obvious that the parameter p−/cell/generation has lost its significance under such conditions because the p+ cells no longer multiply. The following parameter is proposed: p−/ml/optical density unit, which measures only the p-cells at each culture period. Additionally, it enables two different cultures to be compared for their plasmid loss. This parameter is calculated according to the following formula:

$$p-/ml/OD = [1-(\%p+/100)] \times \text{viable cells}/ml/OD.$$

Finally, if this parameter is expressed on the basis of the total number of cells (which is $4 \times 10^8$ under the present conditions), it is possible to obtain the percentage of (Fp−) cells in the culture and to determine the degree of contamination of the culture with p− cells at each period. Fp− is calculated as follows:

$$Fp- = 4 \times 10^8 \, c/ml/OD \times 100(p-/ml/OD).$$

Fp− is an objective parameter which makes it possible to decide whether a culture intended for the production of a molecule is sufficiently pure to make it worthwhile to develop it further and which makes it possible to compare different plasmids with one another under the conditions of induction.

In the inductions described in the following examples, the number of viable cells and the percentage of p+ will be determined and then p/ml/OD and Fp will be calculated. These data will be presented in the form of tables.

EXAMPLE 9

Induction of Hirudin

The results for hirudin induction will be presented, first with a vector containing the ampicillin resistance gene and then with the vector which also contains the dapD gene.

1) Stability of Plasmids a) Induction of hirudin expression in a vector which contains the ampicillin resistance gene (TGE900/pTG720) in an LB medium at 37° C.

Typical results for TGE900/pTG720 are given in Table 3.

TABLE 3

Stability parameters for the plasmids during hirudin expression at 42° C. in TGE900/pTG720

| Time in hours | c/ml/OD | % p+ | p−/ml/OD | Fp−(%) |
|---|---|---|---|---|
| 0 h | $8.3 \times 10^7$ | 100 | $<1.7 \times 10^6$ | <0.4 |
| 1 h 30 | $2.4 \times 10^8$ | 100 | $<4.8 \times 10^6$ | <1.2 |
| 3 h | $2.1 \times 10^8$ | 96 | $8.4 \times 10^6$ | 2.1 |
| 4 h 30 | $4.7 \times 10^7$ | 82 | $8.5 \times 10^6$ | 2.1 |
| 5 h 30 | $1.8 \times 10^7$ | 48 | $9.4 \times 10^6$ | 2.35 |
| 7 h | $2.8 \times 10^7$ | 20 | $2.2 \times 10^7$ | 5.5 |

It is seen that after 3 hours, the number of viable cells per OD unit decreases concurrently with the proportion of p+ cells. After 5 h 30 min, Fp− (% of p− cells relative to the total number of cells) is of the order of 2.35%. After 7 hours, this number will have doubled and it is probable that this is due to the growth of the p− cells only.

b) Induction of hirudin expression in a vector which contains the dapD gene (TGE7615/pTG771) in an LB medium at 37° C.

The results given in Table 4 are comparable to those obtained for pTG720.

TABLE 4

Stability parameters for the plasmids during hirudin expression at 42° C. in TGE7615/pTG771

| Time in hours | c/ml/OD | % p+ | p−/ml/OD | Fp−(%) |
|---|---|---|---|---|
| 0 h | $3.4 \times 10^6$ | 99.8 | $7.7 \times 10^5$ | 0.2 |
| 1 h 30 | $2.1 \times 10^7$ | 99.2 | $1.7 \times 10^5$ | 0.04 |
| 3 h | $9.7 \times 10^6$ | 100 | $<1.0 \times 10^5$ | <0.025 |
| 4 h | $9.3 \times 10^6$ | 100 | $<8.0 \times 10^4$ | <0.005 |
| 5 h | $7.5 \times 10^6$ | 98 | $1.5 \times 10^5$ | 0.04 |

It is seen from Table 4 that despite a mortality comparable to that recorded for TGE900/pTG771, the loss of plasmid (%p+) is low (98% p+ after 5 hours), which is also the case for the absolute quantity of p− cells (p−/ml/OD). The quantity of Fp− after 5 hours is 0.04%, which is 10 times less than that in the case of pTG720 at the same period. This demonstrates the greater stability of pTG771 compared with pTG720. It should be pointed out that in an induction experiment pTG771 does not form tetramers and its loss is supposed to be less than that determined over 170 generations at 30° C. (see Table 2).

The results show a greater stability of the plasmid pTG771 compared with pTG720.

2) Plasmid Content

Plasmids pTG720 and pTG771 were isolated at different times during the induction. In general, in the initial stages of induction, during the exponential phase, a low plasmid content per cell is observed, which increases substantially with time. Hirudin is produced during this period.

It is interesting to note that this increase in plasmid content occurs in a population in which more than 95% of cells are dead.

3) Activity Induced

The hirudin activities produced from pTG720 and pTG771 are not significantly different. The values (in antithrombin units, ATU) are 2720 ATU/1/OD for pTG720 and 2380 ATU/1/OD for pTG771, after 5 hours of induction.

In conclusion, it may be stated that pTG771 shows an increased stability relative to pTG720, while maintaining the same production capacity and the same properties with respect to increasing its copy number as pTG720, at the end of the exponential phase.

EXAMPLE 10

Induction of Interferon-gamma

The data for interferon-gamma induction are presented in the same way as those of hirudin.

1) Stability of Plasmids a) Induction of interferon-gamma expression in a vector containing ampicillin resistance gene (TGE900/pTG40) in an LB medium at 42° C.

The results given in Table 5 show that the loss of plasmids is comparable to that for pTG720, and that Fp− rises to 6% after 5 hours. However, unlike pTG720, the loss of viability is quicker and a minimum value for the number of viable cells is already reached after 3 hours (as compared with 5 hours observed in the case of pTG720); additionally, the p− cells present in the culture remain viable and are already dividing significantly after 3 hours, and contribute 6% to this Fp− after 5 hours.

TABLE 5

Stability parameters for the plasmids during interferon expression at 42° C. in TGE900/pTG40

| Time in hours | c/ml/OD | % p+ (No. of colonies tested) | p−/ml/OD | Fp−(%) |
|---|---|---|---|---|
| 0 h | | | | |
| 1 h 30 | $1.8 \times 10^6$ | 100 (202/202) | $<10^6$ | <1 |
| 3 h | $6.6 \times 10^6$ | 10 (2/20) | $6.0 \times 10^6$ | 1.5 |
| 5 h | $2.5 \times 10^7$ | 2.7 (10/366) | $2.4 \times 10^7$ | 6 |
| 6 h | $4.3 \times 10^7$ | 1.7 (11/645) | $7.3 \times 10^7$ | 18 |
| 8 h | $1.3 \times 10^8$ | 0.9 (4/465) | $1.3 \times 10^8$ | 32 | b) Induction of interferon expression in a vector containing the dapD gene (TGE7615/pTG7671) in LB at 42° C.

The data for a TGE7615/pTG7671 induction at 42° C. in LB appear in Table 6. It is observed that maximum mortality is not reached until 5 hours have elapsed and that at this period, although %p+ is comparable to that in the case of pTG40 (10%), the number of p− cells (p−/ml/OD) is one fifth that obtained after 3 hours in the case of pTG40. In fact, after 5 hours, Fp− is 0.3% whereas Fp− for pTG40 is already 6% after this period. Therefore, there is a difference of a factor of 20, which is a reflection of the increased stability of pTG7671, which observation confirms the stability data at 30° C. (see Table 1).

TABLE 6

Stability parameters for the plasmids during interferon expression at 42° C. in TGE7615/pTG7671

| Time in hours | c/ml/OD | % p+ (No. of colonies tested) | p−/ml/OD | Fp−(%) |
|---|---|---|---|---|
| 0 h | $1.7 \times 10^8$ | 100 (50/50) | $<3.8 \times 10^6$ | <1 |
| 1 h 30 | $1.35 \times 10^8$ | 100 (50/50) | $<2.7 \times 10^6$ | <1.5 |
| 3 h | $4.2 \times 10^7$ | 100 (50/50) | $<8.4 \times 10^5$ | <0.2 |
| 5 h | $1.3 \times 10^6$ | 12 (6/50) | $1.1 \times 10^6$ | 0.3 |
| 6 h | $2.2 \times 10^6$ | 5 (5/100) | $2.1 \times 10^6$ | 0.5 |

Under conditions of TGE7615/pTG7671 induction at 42° C., the stability of the plasmid is practically identical in the selective and the non-selective media, the stability of pTG7671 being very high even in the absence of selection. Plasmid loss is therefore reduced to a level which is very satisfactory and compatible with production on an industrial scale.

2) Plasmid Content

Analysis of plasmid content on agarose gel shows that the strains transformed by the plasmids pTG40 and pTG7671 contain equal quantities of material and that this plasmid content per cell increases with time during the induction.

3) Selection of p+ cells containing the dapD gene

In order to demonstrate the selective capacity of the dapD system taking into account the growth of p−cells, which will no longer be generated as soon as the major part of cells have lost their viability, an induction is carried out, during which the culture is diluted by a factor of 5, three times, at 2-hourly intervals, after which this culture is allowed to reach a stationary phase. The results for TGE7615/pTG7671 induction at 42° C. are presented in Table 7 for growth in a selective medium and in Table 8 for growth in a non-selective LB + DAP medium.

TABLE 7

Stability parameters for the plasmids during interferon expression at 42° C. in TGE7615/pTG7671 in a selective LB medium

| Time in hours | c/ml/OD | % p+ (No. of colonies tested) | p−/ml/OD | Fp−(%) |
|---|---|---|---|---|
| 0 h | $3.8 \times 10^7$ | 100 (50/50) | $<6 \times 10^5$ | <0.2 |
| 2 h | $8.3 \times 10^7$ | 97 (74/76) | $1.4 \times 10^6$ | 0.4 |
| 4 h | $<10^6$ | | | |
| 6 h | $<10^6$ | | | |
| 9 h | $3.7 \times 10^6$ | 100 (60/60) | $<3.7 \times 10^4$ | <0.01 |

TABLE 8

Stability parameters for the plasmids during interferon expression at 42° C. in TGE7615/pTG7671 in an LB + DAP medium

| Time in hours | c/ml/OD | % p+ (No. of colonies tested) | p−/ml/OD | Fp−(%) |
|---|---|---|---|---|
| 0 h | $5.5 \times 10^7$ | 100 | $<1.2 \times 10^6$ | <0.3 |
| 2 h | $9.9 \times 10^7$ | 99 (74/75) | $1.3 \times 10^6$ | 0.3 |
| 4 h | $<10^6$ | | | |
| 6 h | $<10^6$ | | | |
| 9 h | $1.7 \times 10^7$ | 5 (5/100) | $1.6 \times 10^7$ | 4 |

It is observed in Table 8 that, after 9 hours of induction, in the selective LB medium all the viable cells contain the plasmid (the presence of the plasmid is confirmed by mini preparation from 30 colonies out of a total of 60 positive colonies in an LB medium and identification of the plasmid by agarose gel electrophoresis). In contrast, in the non-selective medium, the viability is 5 times as great, but the culture contains only 5% of the cells containing the plasmid. This greater viability in LB+DAP medium than in LB medium shows the growth of p− cells in the medium to which DAP has been added and a fortiori the mortality of the p− cells in the selective medium. Therefore, the LB medium enables an effective counter-selection of p− cells to be carried out.

4) Interferon Production pTG7671 retains the same interferon-gamma production capacity as the original plasmid pTG40.

EXAMPLE 11

Deletion of the dapD gene from the chromosome of the bacterium

Sub-cloning of the dapD gene on 2 PstI fragments

Plasmid pDB6 and M13mp8 are cut with PstI and ligated. The M13s containing the 5' end and the 3' end of the gene are screened with oligonucleotides specific to these regions, TG596 (GCGCTTAATAAC-GAGTTG) and TG598 (TGTGCATACTTTAGTC) respectively. The candidates SB96 and SB98 are chosen, and the insertion of the desired fragments confirmed by sequencing. (See diagram in FIG. 6).

Introduction of an EcoRI site into the 5' and 3' ends of the dapD gene

The EcoRI sites are introduced into SB96 and SB98 by point mutation:
into SB98 with the oligonucleotide TG597:

which pairs with the 3' region of the end of the gene, but before an assumed transcription terminator; and
into SB96 with the oligonucleotide TG620:

which pairs with the 5' region upstream of the assumed promoter for the dapD gene.

The transformants are analysed with the same probes as those used for introducing the EcoRI sites. The presence of this EcoRI site is confirmed by a DNA mini-preparation and then by sequencing the M13 candidates chosen (see drawing in FIG. 7).

Construction of a deletion vector

The kanamycin resistance gene of plasmid pUC-4K (sold by Pharmacia) is recovered in the form of an EcoRI fragment. The M13TG597 and 620 are cut with EcoRI and PstI, which releases the 3' end of the dapD gene (without the assumed terminator) and the 5' end of the gene (without its assumed promoter) respectively.

The cloning vector pTG192 (described in Example 2a) is cut with PstI.

All these fragments are ligated. After the transformation of 5K cells and spreading on an LB medium+ampicillin 0.1 mg/ml+kanamycin 0.02 mg/ml, the colonies are screened with oligonucleotide TG596.

One construction was selected: pTG47. Its structure is analysed by a DNA minipreparation and the orientation of the kanamycin resistance gene is determined by digesting the plasmid with HindIII, which releases 2 bands of sizes 5.3 kb and 4.0 kb. The orientation of kanamycin resistance gene in pTG47 is the same as that of the dapD gene in pDB6 (in the other orientation, beads of sizes 4.9 kb and 4.4 kb would have been obtained).

The diagram for pTG47 is shown in FIG. 8.

Deletion of the DapD Gene from the Chromosome

Deletion of the dapD gene of the chromosome from an intermediate strain.

RH5345 cells, the competence of which amounts to $2.5 \times 10^{-7}$ transformants/$\mu$g of DNA of pTG47, are transformed by the plasmid pTG47 previously cut with KpnI and BglII (see FIG. 8).

This digestion releases a fragment which contains the flanking regions of the dapD gene, the gene itself being replaced by the kanamycin resistance gene.

After spreading on an LB medium+DAP+kanamycin 0.01 mg/ml, 9 candidates are selected: TGE721 to TGE729, the dap$^-$, kan$^R$ phenotype of which is confirmed.

The absence of the dapD gene is confirmed after transformation of these strains by pTG764, by their capacity to multiply in the LB medium.

Deletion of the DapD Gene from the Strains TGE901 and N5969

The dapD deletion of the strain TGE721 is then transduced into strains TGE901 and N5969 with the phage transducer P1vir/TGE721, and the dap$^-$ recombinants selected by their resistance to 0.01 mg/ml of kanamycin.

The candidates chosen are TGE7213, 7214 and TGE7303 respectively. For one candidate, TGE7214, the ile, val, his requirements of the parent strain, TGE901, in addition to the dap$^-$ kan$^R$ character, were confirmed on suitable media.

EXAMPLE 12

Confirmation of the deletion of the Dap Gene in Different Strains by Chromosome Blotting.

The various strains below were analysed:
the parent strains TGE901 and RH5345, dapD$^+$,
the deleted strains TGE7213 and 7214,
the parent strain RL58 which was used to introduce the dapD$^-$ mutation into TGE901, and the dapD$^-$ mutant, TGE7615, derived therefrom, and
a GC4540 strain which is resistant to kanamycin by the integration of Tn5, whereas in TG . . . strains, the kanamycin resistance gene is derived from Tn903 (the 2 genes should not give cross hybridization owing to lack of homology: Beck et al. 1982).

The choice of restriction enzymes is based on the sequence of pDB6; a cut with:

BamHI and HindIII releases a 9-kb chromosomal fragment containing the dapD gene and its flanking regions, in the case of wild strains; in the case of deleted strains, the resistance gene must be released by digestion with BamHI and cut into 2 fragments by digestion with HindIII; and PstI releases 2 fragments, each containing a portion of the dapD gene (2.8 kb from the 5' region and 3.4 kb from the 3' region) for the wild strains; in the case of the deleted strains, digestion with PstI releases the kanamycin resistance gene and the 2 flanking regions (a 2.4-kb fragment on the 5' side and a 2.8-kb fragment on the 3' side) (see FIGS. 6 and 8).

Probes were chosen in order to reveal the dap gene or its flanking regions or the kan$^R$ gene:

in order to probe the kanamycin resistance gene, an EcoRI fragment of pTG47 which contains only this resistance gene (FIG. 8) is isolated; in order to probe the dapD gene, a 2.4-kb EcoRI fragment of M13TG620 which contains only the 5' region of the dapD gene and which must be completely deleted in TGE721, 7213 and 7214 (FIG. 7) is employed; and in order to probe the chromosome, a KpnI-BglII fragment of pTG47 which contains the kanamycin resistance gene and the 2 regions (the 5' and the 3' sides) of the chromosome which flanks the dapD gene (FIG. 8) is employed.

Therefore, revelation of the following is expected:
in the wild strains, a 2.8-kb band corresponding to the 5' region of the dapD gene and a 3.4-kb band corresponding to the 3' region of this gene (FIG. 6); and
in the deleted strains, the kanamycin resistance gene, the 5' region flanking the dapD gene which still exists (2.4 kb) and the 3' region flanking the dapD gene which still exists (2.8 kb) (FIG. 8).

Demonstration of the Incorporation of the Kanamycin Resistance Gene

The chromosomal DNAs of GC4540, TGE7213, TGE7214 and TGE901, cut with PstI or BamHI and HindIII were compared and probed with the EcoRI fragment of pTG47.

PstI releases the 1.3-kb band; a BamHI and HindIII restriction gives 2 fragments of 0.7 kb and 0.6 kb for the deleted strains only. No band is revealed in TGE901 or in GC4540 (FIG. 9A).

These results prove that the kanamycin resistance gene is incorporated into the chromosome of the deleted strains and that this gene originates from pUC-4K.

Demonstration of the deletion of the dapD gene from the chromosome

The chromosomal DNAs of GC4540, TGE7213, 7214 and TGE901 are compared with, as controls, M13TG620, M13TG597, the BamHI-HindIII fragment of pDB6 and the same fragment cut with PstI (FIG. 6).

The chromosomal DNAs are cut with PstI or BamHI and HindIII.

The M13TG620 cut with EcoRI is isolated from the band specifically containing the 5' side of the dapD gene in order to use it as probe (FIG. 9B).

After digestion with PstI, it is seen that in the wild strains, a 2.8-kb band corresponding to the 5' region of the dapD gene and also an unexpected 1.7-kb band are revealed.

After digestion with BamHI and HindIII, an approximately 12-kb band which is larger than the band (9 kb) originating from pDB6 is revealed. Furthermore, an additional 2.5-kb band is also present in the wild strains (FIG. 9B).

For the deleted strains, no significant homology is apparent in any digestion fragment.

These observations show that:

a probe which covers the 5' portion of the dapD gene does not reveal any band in the chromosome of strains TGE7213 and 7214, which demonstrates the deletion of the 5' side of this gene; and in the wild strains, as a second band specific for the dapD gene is revealed in addition to the expected band it seems that this gene is duplicated in these strains.

As a duplication of the dapD gene was unexpected, we have confirmed this duplication in some wild strains and confirmed the deletion of the dapD gene from the 3' side in addition to the 5' side.

The same chromosomal and control DNAs are employed after digestion with PstI (FIG. 8).

The probe is pTG47 cut with KpnI and BglII. In addition to the bands predicted above, this probe must reveal at least a 1.7-kb band. In fact, pTG47 contains 300 bp and 100 bp homologous to the dapD gene, from the 5' side and the 3' side respectively, which must be revealed in the deleted strains.

FIG. 9C shows that:

2.8-kb and 2.4-kb bands are revealed in the deleted strains and 3.4-kb and 2.8-kb bands in the wild strains; additionally, a 1.3-kb band corresponding to the kanamycin resistance gene is revealed. This proves the deletion in strains TGE7213 and 7214; and less intense bands, due to the duplicated dapD gene, are also revealed in the wild strains only. As it is known that the 1.7-kb band is revealed with the 5' portion, the 2.1-kb band must originate from the 3' side. This proves that these strains indeed contain a duplication which has disappeared in the deleted strains.

The chromosomal DNA cut with PstI of strains RH5345 and RL58, and the dapD⁻ mutant obtained by conjugation of RL58 with TGE901 were compared. These DNAs were probed with the KpnI, BglII fragment isolated from pTG47 which contains the kanamycin resistance gene (which should not reveal anything) and the regions flanking the dapD gene. FIG. 9D shows that in RH5345, only the 3.4 and 2.8-kb bands are revealed and not the bands due to the duplication of the gene, which are present in GC4540 or TGE901. Additionally, only a 7-kb band is observed for RL58 and TGE7615, which indicates loss of a PstI site; this proves that these 2 mutants are identical and are affected at least in the PstI site of the dapD gene.

In conclusion, these experiments show that: strains
  TGE7213 and 7214 are deleted for the dapD gene and they contain the kanamycin resistance gene;
the dapD⁻ mutation of RL58 and TGE7615 is present at least at the PstI site of the dapD gene; and some strains of *E. coli* have a duplication of the dapD gene and this duplication is not present in the deleted strains.

As the 2 dapD genes of the recipient strain are successfully deleted by transduction, it may be concluded that the duplicated gene must be close (at less than 2' on the chromosomal map of *E. coli*) to the first dapD gene.

EXAMPLE 13

Cloning of the cer gene

The cer gene is recovered from the Col E1 plasmid, the sequence for which has been published by Chan et al. (1985), in the form of a 1.85-kb HaeII fragment.

The HaeII fragment is then cut with HpaII, treated with Klenow and a 0.4-kb band is recovered. The M13-mp130 is cut with EcoRV and treated with phosphatase. The 0.4-kb fragment of Col E1 is ligated to M13mp130 and it is introduced into the strain JM103. The presence of the Col E1 cer fragment was confirmed by sequencing the 0.4-kb band released by cutting with SmaI and HindIII.

The cer gene inserted into the polylinker of M13mp131 is then isolated after digestion with SmaI and HindIII and ligated to the pTG720 vector (carrying the hirudin gene, FIG. 2) cut with BglII and treated with Klenow. The resulting plasmid is pTG720cer.

EXAMPLE 14

Construction of cloning vectors containing the cer gene and the dapD gene

Inversion of the orientation of the M13mp131 polylinker in a vector coding for ampicillin resistance The pTG192 (FIG. 1) is cut with EcoRI and BglII in order to release the M13mp131 polylinker and is shortened by HaeIII digestion. A plasmid carrying the ampicillin resistance gene, for example pTG730 (expression vector of hirudin, described in French Patent 86/16,723) is employed; this plasmid is cut with BglII and EcoRI and ligated to the EcoRI-BglII fragment of pTG192. In this way, the expression block comprising the P$_L$ and the hirudin structural gene of pTG730 are lost, being replaced with the M13mp131 polylinker. This new plasmid is called pTG790 (FIG. 10).

Introduction of the Cer Fragment Into the Cloning Vector pTG790 is cut with SstI and KpnI and treated with phosphatase. The fragment resulting from this digestion is ligated to pTG720cer, cut with SstI and KpnI (which releases the cer fragment) and shortened by BglII digestion. The resulting vector, pTG792, contains the cer fragment (FIG. 11).

Introduction of the dapD gene into a vector containing the cer fragment pTG792 is cut with EcoRI, treated with Klenow and phosphatase. The resulting fragment is ligated with the 1.3-kb AluI fragment resulting from pDB6 which contains the dapD gene (FIG. 6). 2 plasmids, pTG7922 and pTG7923, result therefrom, and differ only by the orientation of the dapD gene located between 2 EcoRI sites. For pTG7922, the promoters for the 3 genes, replication origin, ampicillin resistance and dapD are oriented in the same way (FIG. 12).

Deletion of the Ampicillin Resistance Gene

The following constructions have a multiple aim:
to delete the ampicillin resistance gene from vectors containing the dapD gene;
to obtain a dapD cloning vector containing the cer gene;

to obtain a dapD cloning vector which contains the M13mp131 polylinker (minus the EcoRV site, used for the cloning of cer); and to obtain a dapD vector with a single EcoRI site.

A PstI fragment is recovered from pTG7922 and pTG7923 containing, respectively, the 3' and 5' portions of the dapD gene as well as the cer gene in order to introduce it into a dap vector containing an analogous fragment but without any EcoRI or AvaI site, or cer. The analogous vectors are respectively pTG767 and pTG766 described above.

The pTG7922 and pTG7923 are cut with PstI, shortened by BglII digestion and ligated respectively to pTG767 and pTG766 cut with PstI and treated with phosphatase. The cloning vectors which result therefrom are pTG769 and pTG768 respectively (pTG769 is shown in FIG. 13).

EXAMPLE 15

Application of the dap model to the construction of expression vectors for catechol 2,3-oxygenase ($C_{2,3}O$).

Vector without BamHI site upstream of $C_{2,3}O$

The structural gene for $C_{2,3}O$ is recovered from pTG444, to be introduced into the dap vector pTG7671 (described above).

pTG444 is identical to pTG445 described by Zukowski et al. (1984) except for a non-regenerated XmaIII site. The pTG444 is cut with BamHI and HindIII and ligated to pTG769 cut with BamHI and HindIII and treated with phosphatase. The resulting plasmid, called pTG7401, does not contain the structural gene for $C_{2,3}O$.

pTG7671 contains 2 BglII sites: a site upstream of $P_L$ forming part of the polylinker and a site downstream of $P_L$ located in the ribosome binding site, upstream of the structural gene for interferon-gamma. The pTG7671 is cut with BglII and shortened by KpnI digestion. The resulting mixture is ligated to pTG7401, cut at its polylinker, with BglII and BamHI and treated with phosphatase. The BglII site is reconstituted by this ligation, but the BamHI site ligated to the BglII site is lost. Two orientations of $P_L$ with respect to the structural gene for $C_{2,3}O$ are possible. In order to distinguish the construction in which $C_{2,3}O$ is under the control of $P_L$, cutting is carried out with BamHI and BglII (in fact, for the orientation desired, a BamHI site is present near the BglII site and in practice, the digestion will give only a 4.3-kb band; in the other orientation, the digestion releases a 3.9-kb band and a 0.4-kb band.

The plasmid chosen, pTG7407, having $C_{2,3}O$ under the control of $P_L$, has a structure close to pTG7406 described later (compare with FIG. 14), however, it has lost its BamHI site upstream of $C_{2,3}O$.

Vector with a BamHI site upstream of $C_{2,3}O$ pTG769 is cut with BglII and BamHI, treated with phosphatase and ligated with a BamHI-BglII fragment of any expression plasmid (pTG907) which contains $P_L$ and the complete N gene of λ. A construction, pTG7400, results therefrom, which may be identified by a BamHI and BglII cut which releases 2 bands, of 2.6 kb and 1.3 kb. This construction contains the $P_L$ and the complete N gene.

The pTG7400 is then cut with HpaI and a BamHI linker, CCGGATCCGG (sold by BRL), which has been phosphorylated and hybridized, is inserted therein.

This gives pTG7402 which has lost its HpaI site but which contains 2 BamHI sites.

The pTG7402 is cut with BamHI and religated to give pTG7404. By this procedure, a BamHI site is removed and the N gene is truncated.

Introduction of the $C_{2,3}O$ gene into a dap-cer vector

The pTG7402 is cut with BamHI and HindIII, treated with phosphatase, and the BamHI-HindIII fragment of pTG444 is introduced therein to give pTG7406 (see FIG. 14). It differs from pTG7407 in that the $C_{2,3}O$ gene may be removed by a BamHI-HindIII cut so as to recover the fragment introduced from pTG444.

Expression of $C_{2,3}O$ in dap$^-$ E. coli strains transformed by the plasmid pTG7407

The expression of the $C_{2,3}O$ gene in the bacteria TGE7213/pTG7407 was determined at 30° C. after 4 h and 7 h of culture and during induction at 42° C. after 4 h and 7 h. For each determination, a sample is harvested from the culture and centrifuged; the pellet is washed and taken up with phosphate buffer (as described by Zukowski et al., 1983) and then treated with ultrasound 3 times for 20 seconds each.

After centrifuging for 10 min at 10,000 g, the pellet is considered as the insoluble fraction (P) and the supernatant as the soluble fraction (S).

The proteins present in each fraction are analysed by electrophoresis on SDS polyacrylamide gel. The bands are visualized by staining with Coomassie blue. The results are presented in FIG. 15. The intensity of the band for MW 35,000 is noted, especially after 7 h of induction at 42° C. The "scanning" of the gel gives approximately 64% and 75% of $C_{2,3}O$ in fractions S and P respectively.

In the richer sample (S, 7 h at 42° C.), the specific activity of $C_{2,3}O$ is determined (according to the method described by Zukowski et al., 1983), by adding catechol as substrate. A specific activity of 28 to 35 U/mg is measured.

The specific activity of a pure enzyme preparation being 280 U/mg, the extracts analyzed contain approximately 12% of active $C_{2,3}O$.

EXAMPLE 16

Introduction of the Cer Fragment Into an Expression Vector of Interferon-Gamma.

The pTG7671 described above is cut at its polylinker with SstI (identical to SacI) and KpnI and then treated with phosphatase and ligated to fragments pTG720cer cut with SstI and KpnI. After transformation in TGE7615, one candidate, pTG7675, which releases 2 fragments of 400 bp and 3.4 kb after digestion with SstI and KpnI (FIG. 16) is chosen.

EXAMPLE 17

Demonstration of the Stability of the Plasmids During the Induction of Interferon-Gamma Expression a) Induction of interferon-gamma expression in LB medium at 42° C. for a vector carrying the ampicillin resistance gene: TGE901/pTG40.

The results are given in Table 9. The total number of cells/OD unit/ml is determined in order to ensure that the loss of viability is a true phenomenon and not, for example, a change in cell volume. These data are also given in Table 9. Fp$^-$ was defined in the main patent and relates the number of p⁻ cells to the total number of cells present at a given time.

It will be noted that Fp⁻ after 7 h 30 min of induction reaches a value of approximately 2%. Therefore, it is less than in the previous experiment (see Example 10), which can be attributed only to a difference in the structure of the plasmid pTG40 in these 2 experiments: in fact, although the quantity of plasmid is the same at different times of induction, in the first experiment the plasmid was in the dimeric form, whereas in the experiment described here it is mainly in the monomeric form (as shown by analysis on gel). The condition of the plasmid does not affect interferon-gamma production, but illustrates conclusively the loss of stability if the monomeric form of a plasmid is not maintained.

b) Induction of interferon-gamma expression in a strain mutated for the dap gene and transformed by a vector containing the dapD gene and the cer gene, TGE7615/pTG7675

The results are given in Table 10. The total number of cells/OD unit/ml are determined; there is no marked difference with TGE901/pTG40. A real loss of viability is thus confirmed: after 7 h 30 min of induction, only 0.02% of the culture remains viable. This should be compared with TGE901/pTG40 in which case the value obtained is 2.4%. This manifests itself in Fp⁻, which is decreased by a factor of 1000 in the case of TGE7615/pTG-7675 compared with TGE901/pTG40. Nevertheless, some p⁻ cells still remain, which appear at the end of induction. The plasmid content has the same features as before, i.e. increase in the copy number at the end of growth, but the multimeric forms, which are present in variable numbers with the plasmids without cer, are almost absent in this case. The interferon-gamma production is slightly greater than that obtained with pTG40.

c) Induction of interferon-gamma expression in a host cell deleted for the dapD gene and transformed by a vector containing the dapD gene and cer, TGE7213/pTG7675

The results are given in Table 11. The conclusions are identical to those drawn from the comparison between TGE901/pTG40 and TGE7615/pTG7675: the mortality reaches a factor of $3.5 \times 10^{-4}$, and the value for total number of cells/OD unit/ml does not vary significantly during the induction. In contrast, even after 7 h 30 min of induction, p⁻ cells do not appear (after 24 h, the entire culture became p⁻ in the case of TGE901/pTG40 and remained 100% p⁺ in the case of TGE7213/pTG7675). The plasmid content is comparable to that of TGE7615/pTG7675 in the absence of multimers. Interferon-gamma production is slightly greater than that obtained with TGE7615/pTG7675.

TABLE 9

Induction of TGE901/pTG40 at 42° C. in LB medium

| | O.D. 600 nm | c/ml/O.D. | total number of cells/ml/O.D. | Fp⁻ |
|---|---|---|---|---|
| 0 h 00 min | 0.370 | $3.9 \times 10^8$ | | <1.4% |
| 1 h 00 min | 1.29 | $3.8 \times 10^8$ | $6.5 \times 10^8$ | |
| 2 h 00 min | 1.67 | $3.0 \times 10^7$ | $7.2 \times 10^8$ | 0.03% |
| 3 h 00 min | 2.13 | $2.7 \times 10^6$ | | 0.11% |
| 4 h 00 min | 2.42 | $2.8 \times 10^6$ | $6.7 \times 10^8$ | 0.23% |
| 6 h 15 min | 2.89 | $7.0 \times 10^6$ | $6.5 \times 10^8$ | 0.70% |

TABLE 9-continued

Induction of TGE901/pTG40 at 42° C. in LB medium

| | O.D. 600 nm | c/ml/O.D. | total number of cells/ml/O.D. | Fp⁻ |
|---|---|---|---|---|
| 7 h 30 min | 3.08 | $9.5 \times 10^6$ | | 1.73% |

NOTE: Fp⁻ is the percentage of p⁻ cells over the total number of cells present at a given time.

TABLE 10

TGE7615/pTG7675 at 42° C. in LB medium

| | O.D. 600 nm | c/ml/O.D. | total number of cells/ml/O.D. | Fp⁻ |
|---|---|---|---|---|
| 0 h 00 min | 0.310 | $3.5 \times 10^8$ | | |
| 1 h 00 min | 1.07 | $3.3 \times 10^8$ | $4.7 \times 10^8$ | |
| 2 h 00 min | 1.64 | $1.5 \times 10^8$ | $5.1 \times 10^8$ | |
| 3 h 00 min | 2.31 | $1.44 \times 10^7$ | | |
| 4 h 00 min | 2.67 | $7.1 \times 10^6$ | $7.9 \times 10^8$ | |
| 6 h 15 min | 3.26 | $6.1 \times 10^4$ | $6.1 \times 10^8$ | 0.0017% |
| 7 h 30 min | 3.44 | $6.4 \times 10^4$ | | 0.0018% |

TABLE 11

Induction of TGE7214/pTG7675 at 42° C. in LB medium

| | O.D. 600 nm | c/ml/O.D. | total number of cells/ml/O.D. | Fp⁻ |
|---|---|---|---|---|
| 0 h 00 min | 0.400 | $3.4 \times 10^8$ | | <1.1% |
| 1 h 00 min | 1.25 | $3.7 \times 10^8$ | $5.8 \times 10^8$ | |
| 2 h 00 min | 1.71 | $3.8 \times 10^7$ | $7.1 \times 10^8$ | |
| 3 h 00 min | 2.45 | $3.0 \times 10^5$ | | |
| 4 h 00 min | 3.32 | $6.6 \times 10^4$ | $12.8 \times 10^8$ | |
| 6 h 15 min | 4.25 | $7.3 \times 10^4$ | $5.8 \times 10^8$ | |
| 7 h 30 min | 4.21 | $1.2 \times 10^5$ | | $<6 \times 10^{-4}$% |

EXAMPLE 18

Application of the Dap Model to the Construction of an Expression Vector for Alpha-1 Antitrypsin The PstI fragment containing the alpha-1 antitrypsin expression block, i.e. the phage lamba promoter $P_L$, the truncated N gene, a ribosome binding site and the structural gene for alpha-1 antitrypsin (Arg$^{358}$), originating from pTG2901 (truncated derivative of pTG983, described in Patent 85/07,393) is introduced into pTG792 (described above), cut with PstI and treated with phosphatase.

The resulting expression vector, pTG7913, is then cut with BglII and SstI and the expression block containing the alpha-1 antitrypsin and the cer gene is introduced into pTG767, cut with BglII and SstI and treated with phosphatase.

The resulting plasmid, pTG7914, contains the dapD gene, the cer gene and the alpha-1 antitrypsin expression block (Arg$^{358}$) (FIG. 17).

Deposition of Representative Strains of the Invention

The following strains were deposited at the Collection Nationale de Cultures des Microorganismes (National Collection of Microbial Cultures) (25 Rue du Dr. Roux, Paris):

TGE7615/pTG7671 under the number I-586) on
TGE7615/pTG771 under the number I-585) 25.07.86
TGE7214, dapD gene-deleted coli strain, under the number I-652;
TGE7303, dapD gene-deleted coli strain, under the number I-653;
(the 2 strains are transformed by the plasmid pTG768 which carries the dapD and cer gene); and TGE7214/pTG7407, dapD⁻ strain transformed by the expression plasmid for $C_{2,3}O$, under the number I-655 on 10.03.87.

REFERENCES

1. Jones I. M., Primrose S. B., Robinson A., Ellwood D. C. (1980) Mol. Gen. Genet. 180, 579-584.
2. Nilsson J., Skogman G. (1985) European patent application no. 84850313.2.
3. Skogman G., Nilsson J. (1984) Gene 31, 117-122.
4. Milwa K. Nakamori S., Sano K., Momose H. (1984) Agric. Biol. Chem. 48, 2233-2237.
5. Miwa K., Nakamori S., Sano K. Momose H., (1984) Gene 31, 275-277.
6. Hershberger C. L., Rosteck P. R. (1984) U.S. Pat. No. 4,436,815.
7. Work E. (1950) Nature 165, 74-75.
8. Davis B. D., Dulbecco R., Eisen H. N., Ginsberg H. S., Wood W. B. (2nd Ed. 1973) Microbiology Ed. Harper International p. 72.
9. Dauce-Le Reverend B., Boitel M., Deschamps A. M., Lebeault J-M., Sano K., Takinami K., Patte J-C. (1982) European J. Appl. Microbiol. Biotechnol. 15, 227-231.
10. Richaud C., Richaud F., Martin C., Haziza C., Patte J-C. (1984) J. Biol. Chem. 259, 14824-14828.
11. Hanahan D. (1983) J. Mol. Biol. 166, 557-580.
12. Bollen A., Lathe R., Herzog A., Denicourt D., Lecocq J-P., Demarez L., Lavalle R. (1979) J. Mol. Biol. 132, 219-233.
13. Gottesman M. E., Adhya S., Das A. (1980) J. Mol. Biol. 140, 57-75.
14. Lusky M., Botchan M. (1981) Nature 293, 79-81.
15. Vieira J., Messing J. (1982) Gene 22, 259-268.
16. Lathe R., Kieny M. P., Skory S., Lecocq J-P. (1984) DNA 3, 173-182.
17. Kieny M-P., Lathe R., Lecocq J-P. (1983) Gene 26, 91-99.
18. Bendiak D. S., Friesen J. D. (1981) Mol. Gen. Genet. 181, 356-362.
19. Summers D. J., Sherratt D. J. (1984) Cell 36, 1097-1103.
20. Beck, E., Ludwig, G., Auerswald, E. A., Reiss, B. & Schaller, M. Gene 19, 327-336 (1982).
21. Bendiak, D. S. & Friesen, J. D. Mol. Gen. Genet. 181, 356-362 (1981).
22. Bollen, A., Lathe, R., Herzog, A., Denicourt, D., Lecocq, J. P., Desmarez, L. & Lavallé, R. J. Mol. Biol. 132, 219-233 (1979).
23. Bukhari, A. I. & Taylor, A. L. J. Bacteriol. 105, 844-854 (1971).
24. Chan, P. T., Ohmori, H., Tomizawa, J. I & Lebowitz, J. J. Biol. Chem. 260, 8925-8935 (1985).
25. D'Ari, R. & Huisman, O. J. Bacteriol. 156, 243-250 (1983).
26. Richaud, C., Richaud, F., Martin, C., Haziza, C. & Patte, J. C. J. Biol. Chem. 259, 14824-14828, 1984.
27. Summers, D. K. & Spherratt, Cell 36, 1097-1103 (1984).
28. Zukowski, M. M., Gaffney, D. F., Speck, D., Kauffmann, M., Findeli, A., Wisecup, A. & Lecocq, J. P. Proc. Natl. Acad. Sci. USA 80, 1101-1105 (1983).
29. Zukowski, M. M., Speck, D., Kauffmann, M. & Lecocq, J. P. Genetics and Biotechnology of Bacilli 309-319 (1984).

I claim:
1. An *E. coli* cell wherein the genome comprises a dapD gene inactivated by mutation and which *E. coli* cell is transformed with a plasmid comprising a functional dapD gene.
2. The *E. coli* according to claim 1, wherein said mutation is a deletion mutation.
3. The *E. coli* according to claim 1, wherein said plasmid further comprises a "cer" sequence which maintains the plasmid in a monomeric state.
4. The *E. coli* cell of claim 1, wherein said plasmid further comprises a gene that encodes a heterologous protein operably linked to a promoter.
5. The *E. coli* according to claim 4, wherein said heterologous protein is hirudin, gamma-interferon, catechol 2,3 oxygenase or alpha-antitrypsin.
6. A process for preparing a heterologous protein which comprises the steps of:
    culturing the *E. coli* according to claim 4 in a DAP-free medium containing lysine under conditions such that said heterologous protein is produced; and
    isolating said protein from the culture.

* * * * *